United States Patent
Ko et al.

(10) Patent No.: US 11,523,863 B2
(45) Date of Patent: Dec. 13, 2022

(54) MEDICAL RF APPARATUS AND A METHOD FOR CONTROLLING THE SAME

(71) Applicant: LUTRONIC CORPORATION, Goyang (KR)

(72) Inventors: Kwang Chon Ko, Paju (KR); Richard Howard Cohen, San Rafael, CA (US)

(73) Assignee: LUTRONIC CORPORATION, Goyang (KR)

(*) Notice: Subject to any disclaimer, the term of this patent is extended or adjusted under 35 U.S.C. 154(b) by 1181 days.

(21) Appl. No.: 16/041,593

(22) Filed: Jul. 20, 2018

(65) Prior Publication Data
US 2019/0262066 A1 Aug. 29, 2019

(30) Foreign Application Priority Data
Feb. 26, 2018 (KR) .................. 10-2018-0022812

(51) Int. Cl.
*A61B 18/14* (2006.01)
*A61B 18/12* (2006.01)
*A61B 18/00* (2006.01)

(52) U.S. Cl.
CPC ...... *A61B 18/1477* (2013.01); *A61B 18/1206* (2013.01); *A61B 18/14* (2013.01); *A61B 2018/0047* (2013.01); *A61B 2018/00458* (2013.01); *A61B 2018/00678* (2013.01); *A61B 2018/00702* (2013.01); *A61B 2018/00761* (2013.01); *A61B 2018/00791* (2013.01); *A61B 2018/00875* (2013.01); *A61B 2018/00886* (2013.01); *A61B 2018/00922* (2013.01); *A61B 2018/143* (2013.01); *A61B 2018/1425* (2013.01); *A61B 2018/1475* (2013.01)

(58) Field of Classification Search
CPC . A61B 18/1206; A61B 18/14; A61B 18/1477; A61B 2018/00452; A61B 2018/00458; A61B 2018/0047; A61B 2018/00678; A61B 2018/00702; A61B 2018/00761; A61B 2018/00791; A61B 2018/00875; A61B 2018/00886; A61B 2018/00922; A61B 2018/1425; A61B 2018/143; A61B 2018/1475
See application file for complete search history.

(56) References Cited

U.S. PATENT DOCUMENTS

| | | | | |
|---|---|---|---|---|
| 6,398,779 B1* | 6/2002 | Buysse | ............ | A61B 18/1445 606/34 |
| 8,663,214 B2* | 3/2014 | Weinberg | .......... | A61B 18/1206 606/34 |

(Continued)

FOREIGN PATENT DOCUMENTS

| JP | 2010512181 A | 4/2010 |
|---|---|---|
| JP | 2011529732 A | 12/2011 |

(Continued)

*Primary Examiner* — Michael F Peffley

(57) ABSTRACT

Disclosed herein is a medical RF apparatus using an RF pulse, comprising an RF generator, which generates a test pulse for detecting characteristics of tissue; a monitoring unit, which monitors the change in the information on the tissue state while the test pulse is transmitted to the tissue; and a measurement unit, which determines the tissue characteristics of a patient by comparing the values monitored in the monitoring unit with the reference data; and a method for controlling the same.

20 Claims, 18 Drawing Sheets

(56) References Cited

U.S. PATENT DOCUMENTS

| | | | |
|---|---|---|---|
| 10,582,964 B2 * | 3/2020 | Weinberg | A61B 18/1233 |
| 2004/0193148 A1 * | 9/2004 | Wham | A61B 18/1482 606/40 |
| 2006/0293731 A1 * | 12/2006 | Rubinsky | A61B 18/1477 607/98 |
| 2010/0250209 A1 * | 9/2010 | Pearson | A61B 18/1206 703/2 |
| 2012/0277587 A1 | 11/2012 | Adanny et al. | |
| 2015/0231418 A1 | 8/2015 | Kim | |
| 2016/0066977 A1 * | 3/2016 | Neal, II | A61B 18/18 606/34 |

FOREIGN PATENT DOCUMENTS

| | | |
|---|---|---|
| JP | 2016529923 A | 9/2016 |
| KR | 20030094876 A | 12/2003 |
| KR | 10-2011-0000790 A | 1/2011 |
| KR | 20120099211 A | 9/2012 |
| KR | 10-1269970 B1 | 5/2013 |
| KR | 20150096272 A | 8/2015 |
| WO | 2003103768 A1 | 12/2003 |

* cited by examiner

MEDICAL RF APPARATUS AND A METHOD FOR CONTROLLING THE SAME

CROSS-REFERENCE TO RELATED APPLICATIONS

Priority to Korean patent application number 10-2018-0022812 filed on Feb. 26, 2018, the entire disclosure of which is incorporated by reference herein, is claimed.

BACKGROUND OF THE INVENTION

Field of the Invention

The present invention relates to a medical RF apparatus using an RF pulse and a method of controlling the same, and more specifically, to a medical RF apparatus capable of performing an examination/diagnosis of skin characteristics based on the information on the change in the state of tissue by an RF pulse and a method of controlling the same.

Discussion of the Related Art

The methods for treating tissue using RF energy may be divided into a contact treatment method for treating tissue by transmitting RF energy to the external surface of tissue, and an invasive treatment method in which RF energy is transmitted to tissue by inserting a part or the entirety of an RF electrode into the inside of the tissue. Between these two methods, the invasive treatment method employs a treatment apparatus having a needle, catheter, etc. and an insertion unit with a small diameter, and the treatment is performed by inserting the treatment apparatus into the target site inside of the tissue followed by transmitting the RF energy to the inside of the tissue.

These RF treatment methods are mainly used for surgical treatment such as incision or hemostasis of lesions of the internal organs of the body. Recently, these methods have been used for the treatment of skin lesions such as wrinkle removal, scar removal, and acne treatment by inserting a needle-shaped electrode into the skin followed by transmitting RF energy thereto. This technology is also disclosed in KR Patent Application Publication No. 10-2011-0000790.

In RF treatment methods, once an RF current is applied to tissue through an electrode, the tissue acts as a resistance and generates heat energy RF, and as a result, the tissue undergoes a change and thereby treatment is performed. In particular, even when the same level of energy is delivered to tissue, there may occur deviations such as provision of inappropriate treatment or occurrence of excess treatment according to the state or characteristics of the tissue. Accordingly, there is a need for the development of a technique for determining tissue characteristics by performing an examination on tissue before performing treatment so as to provide an optimal treatment based on the characteristics of the tissue.

Prior Art

SUMMARY OF THE INVENTION

The present invention provides a technique for examining tissue characteristics using an RF energy, and more specifically, a medical RF apparatus capable of examining tissue characteristics including the degree of tissue aging, etc. based on the information on the change in the state of tissue while a test pulse is transmitted, an apparatus for treatment including the same, and a method for controlling these apparatuses.

To achieve the above objects, the present invention provides a medical RF apparatus using an RF pulse, which includes an RF generator, which generates a test pulse for detecting characteristics of tissue; a monitoring unit, which monitors the change in the information on the tissue state while the test pulse is transmitted; and a measurement unit, which determines the tissue characteristics of a patient by comparing the values monitored in the monitoring unit with the reference data.

In particular, the measurement unit may be configured to determine the characteristics of the tissue based on the time required for the tissue to reach the desired change while the test pulse is transmitted.

Specifically, the measurement unit may determine the characteristics of the tissue based on the time required for the desiccation of the tissue while the test pulse is transmitted.

The measurement unit may determine that as the time required is longer the water content of the tissue is higher, whereas as the time required is shorter the water content of the tissue is lower.

In particular, the measurement unit is configured so that the test pulse can be transmitted in a predetermined output pattern and the pulse duration can be maintained until the time point when the tissue reaches the desired change.

Additionally, the monitoring unit is configured to measure the value correlated with the water content of the tissue while the test pulse is transmitted, and the measurement unit is configured to determine the tissue characteristics of a patient by comparing the measured values with the reference data.

Specifically, the monitoring unit is configured to monitor the change in the impedance of the tissue while the test pulse is transmitted, and the measurement unit is configured to determine the characteristics of the tissue based on the time required for the monitored impedance value to reach the target value.

In particular, the measurement unit can determine the characteristics of the tissue based on the time required until the time point when the impedance of the tissue increases at a rate greater than the predetermined rate of change or increases greater than the predetermined value while the test pulse is transmitted.

Alternatively, it is possible that the monitoring unit monitors the change in temperature of the tissue while the test pulse is transmitted, and the measurement unit determines the characteristics of the tissue based on the time required for the monitored temperature value to reach the target value.

Meanwhile, to achieve the above objects, the present invention provides an RF apparatus, which includes an RF generator, which generates a test pulse for detecting characteristics of tissue and a pulse for treatment for treating tissues; a monitoring unit, which monitors the information on the state of the tissue while the test pulse or the pulse for treatment is transmitted; a measurement unit, which determines the tissue characteristics of a patient based on the change in the information on the tissue state being monitored in the monitoring unit while the test pulse is transmitted to the tissue; and a control unit, which controls the parameters of the pulse for treatment by setting the initial parameters of the pulse for treatment by the tissue characteristics of a patient determined in the measurement unit, followed by monitoring the information on the tissue state detected in the monitoring unit while the pulse for treatment is transmitted.

Furthermore, to achieve the above objects, the present invention provides a method for performing an examination, which includes transmitting a test pulse to a site for treatment; monitoring the information on the state of tissue at a site for treatment while the test pulse is transmitted; and determining the tissue characteristics of a patient through the monitoring based on the time required for the desired change in the state to occur in the tissue.

Additionally, such a tissue examination method may further include a step of displaying the determined tissue characteristics through a display unit.

Additionally, such a tissue examination method may be configured to further include transmitting of a pulse for treatment to a site for treatment, in which the initial parameters for the pulse for treatment can be set based on the tissue characteristics determined in the step of determining the tissue characteristics.

The present invention enables the determination of tissue characteristics through the change in tissue state by a test pulse. Accordingly, the present invention has advantages in that the information can be continuously monitored by scoring the tissue state of a patient, and optimal treatment can be performed by selecting parameters for treatment in consideration of the same at the time of treatment.

DETAILED DESCRIPTION OF THE EMBODIMENTS

Hereinafter, a medical RF apparatus according to embodiments of the present invention and a method of controlling the apparatus will be described in detail with reference to the drawings. In the following description, the positional relationship between each constituting element is principally described based on the drawings. Additionally, it should be noted that the drawings may be simplified or exaggerated for the convenience of the description when necessary. Therefore, the present invention is not limited thereto, and it should be obvious that the present invention can be implemented by adding, changing, or omitting various apparatuses.

Hereinafter, the term "medical RF apparatus" includes all of the apparatuses that employ RF energy for medical purposes. The medical RF apparatus may include an RF treatment apparatus for tissue treatment and an RF testing apparatus for testing tissue characteristics, and additionally, may include various apparatuses that employ RF energy for medical purposes.

Hereinafter, the term "RF treatment apparatus" includes all of the apparatuses for treating mammals including humans. The treatment apparatus may include various kinds of apparatuses for treatment by transmitting RF energy for the purposes of improving the states of lesions or tissues. In the following embodiments, explanations are provided being mainly focused on apparatuses for treating skin lesions. However, the present invention is not limited thereto, and it should be understood that the present invention can be applied to various apparatuses used for transmitting RF energy to various lesions including an apparatus for surgically treating lesions in the internal organs of the body.

Hereinafter, the term "RF testing apparatus" includes all of the apparatuses for testing the characteristics of tissues (e.g., health state, collagen content, water content, etc. of tissues) in mammals including humans. The RF testing apparatus includes various apparatuses for testing the characteristics of tissues using an RF pulse, and it should be understood that the RF testing apparatus can be applied to various testing apparatuses for testing the characteristics of various tissues in the organs of the body in addition to skin tissues, as is the case with the treatment apparatuses.

Hereinafter, the term "tissue" refers to a set of cells constituting various internal body organs of animals including humans, and includes various tissues that constitute various internal organs of the body along with skin tissue.

Hereinafter, the term "insertion unit" refers to a constitution of a treatment apparatus that is inserted into the inside of tissue. The insertion unit includes various constitutions, such as a needle, a microneedle, and a catheter, which are comprised of a structure in which an end portion is sharp, long, and thin so that they can penetrate the surface of tissue and be inserted into the inside of the tissue.

Figure 1:
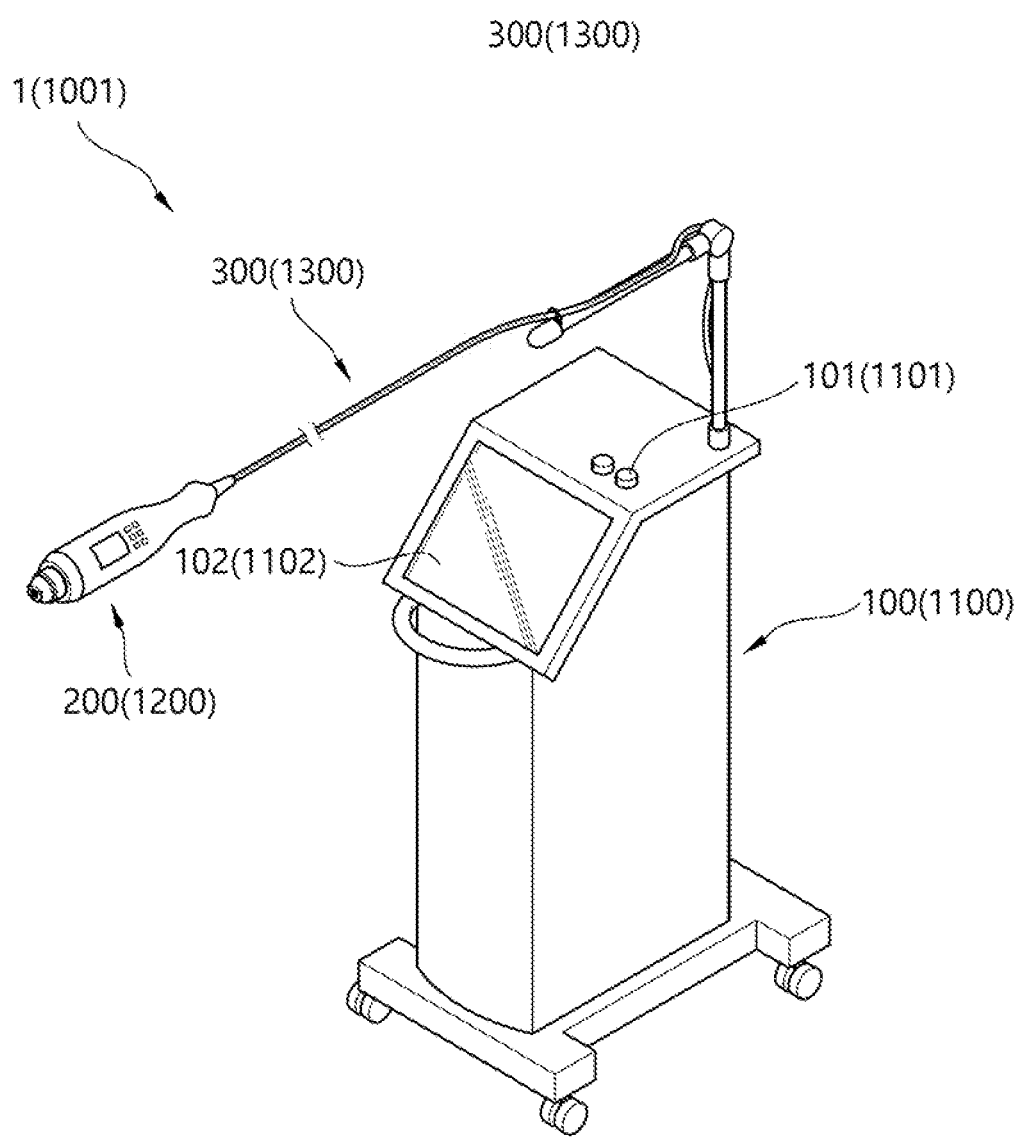
FIG. 1 is a perspective view illustrating a medical RF apparatus according to an embodiment of the present invention.
Figure 2:
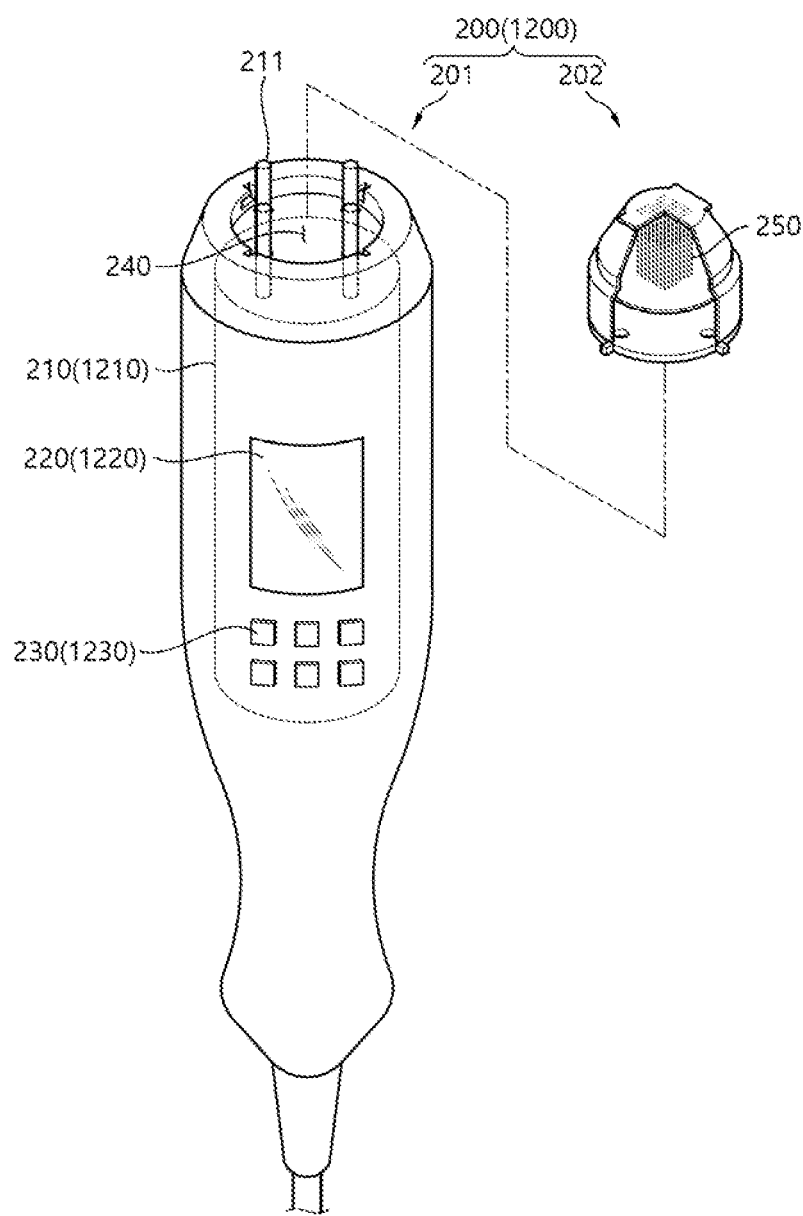
FIG. 2 is a perspective view illustrating a hand piece of the medical RF apparatus of FIG. 1.

Hereinafter, a medical RF apparatus according to a first embodiment of the present invention will be explained with reference to FIG. 1. FIG. 1 is a perspective view illustrating an RF treatment apparatus according to an embodiment of the present invention, and FIG. 2 is a perspective view illustrating a hand piece of the medical RF treatment apparatus of FIG. 1.

As illustrated in FIG. 1, the medical RF apparatus according to the present embodiment is comprised of an RF treatment apparatus, and the RF treatment apparatus is configured to include a main body 100 and a hand piece 200, which a user can hold while performing the treatment.

The main body 100 may be provided with an RF generator 110 therein. The RF generator 110 generates RF energy to be used for treatment. The RF generator 110 is configured to generate RF energy in the form of a pulse rather than a continuous waveform to be transmitted. The RF generator 110 can generate RF pulses of various parameters (e.g., output, pulse duration, pulse interval, frequency, etc.) according to the constitution of a patient, purpose of treatment, site for treatment, etc. The RF pulses generated in the RF generator of the present invention is an RF pulse used for the purpose of treating tissues.

The main body 100 may be provided on its external surface with a switch 101 that controls the operation of the treatment apparatus along with an on/off switch, and a display unit 102 that displays various kinds of information including the operation details of the treatment apparatus. The display unit 102 may be comprised of a touch screen so that a user can directly set the details of treatment through the display unit 102 while simultaneously displaying various kinds of information.

The hand piece 200 is connected to the main body by a connection unit 300. The connection unit 300 is configured so that it can transmit a power source, control signal, etc. necessary for the operation of various kinds of apparatuses of the hand piece 200 from the main body 100. In an embodiment, the RF energy generated in the RF generator 110 of the main body 100 is transmitted toward the hand piece 200 through the connection unit 300. The connection unit 300 may be comprised of a cable that includes various kinds of signal lines, power lines, etc., or may be comprised of a bending structure that can be easily bent by the manipulation of a user.

Meanwhile, the hand piece 200 is a constitution that substantially performs treatment in a site adjacent to the site for treatment, and is configured in a form that a user can hold to use it. Schematically, the hand piece 200 is configured to include an insertion unit 250 which enables an insertion into the inside of tissue to perform the invasive treatment, a driving unit 210 to transport the insertion unit, and a manipulation unit 230 that manipulates the operation details of the insertion unit and the driving unit.

Specifically, as illustrated in FIG. 2, a hand piece manipulation unit 230 and a hand piece display part 220 may be provided on the external surface of a housing constituting the body 201 of the hand piece 200. The hand piece manipulation unit 230 is configured to manipulate on/off of the hand piece, control the insertion depth of the insertion unit 250, or control the size of energy to be transmitted through the insertion unit 250, etc. The display part 220 of the hand piece can indicate the set mode or various kinds of information necessary for treatment to a user. Accordingly, the user can easily figure out the details of treatment through the display part 220 while simultaneously performing the treatment by manipulating the manipulation unit 230 with the hand piece 200 held in the hand of the user.

The driving unit 210 is installed inside of the hand piece 200. The driving unit 210 is configured to selectively insert the insertion unit 250 into the inside of tissue by transporting the insertion unit 250. The driving unit 210 may be formed using various linear actuators such as solenoids, oil/air cylinders, etc., and linear motors, etc. For example, the driving unit in the present embodiment is configured to make a linear movement of the output terminal 211 provided at one end in a longitudinal direction. At the end of the output terminal 211, a plurality of needles corresponding to the insertion unit 250 are arranged, and as the output terminal moves linearly, the insertion unit is configured to protrude and withdraw at one end of the hand piece (one end that comes into contact with the treatment position). As such, by the operation of the driving unit, the insertion unit can be inserted into or withdrawn from the patient's tissue while moving forward/backward.

As described above, the insertion unit 250 is configured to be inserted into the tissue through the tissue surface, and is provided on the hand piece. The insertion unit 250 in the present embodiment is composed of a microneedle which is easy to insert into tissue, however, the insertion unit 250 may additionally be composed of various structures such as a single needle structure, a catheter, etc. In the present embodiment, the microneedle may be those having a diameter in a range of several µm to several thousand µm, and preferably those having a diameter in a range of 10 µm to 1,000 µm.

With respect to the insertion unit 250, a hygiene problem may occur if it is repeatedly used as a constitution to be inserted into the tissue of a patient's body. Therefore, the insertion unit of the present embodiment is composed of a tip module 202 detachable from an end of the hand piece, and is configured to be used by replacing the tip module after the treatment.

In particular, an insertion unit 250 consisting of a plurality of microneedles is installed inside of the tip module 202 and is detachably installed to a recess unit 240 which is provided at one end of the hand piece body. On the opposite surface of the tip module 202, a plurality of holes into which the output terminal 211 described above can be selectively inserted (not shown) are provided. Accordingly, the plurality of microneedles accommodated in the tip module are also configured to be able to advance/withdraw as the output terminal 211 advances/withdraws. Additionally, once the tip module is installed into the recess unit 240, the microneedles in the tip module are electrically connected to the RF circuit within the hand piece thereby being able to transmit RF energy to the inside of the tissue at a site for treatment through the microneedles.

The detailed configuration of the hand piece and the tip module can be implemented in various ways by referring to the configuration disclosed in Korean Patent No. 10-1300123.

Figure 3:
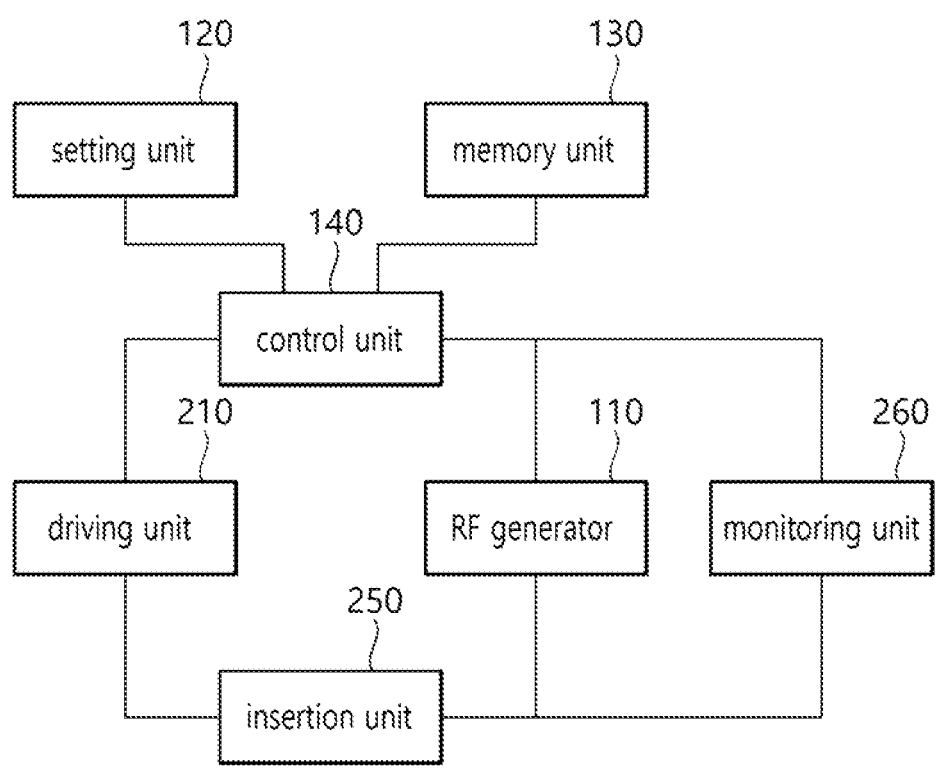
FIG. 3 is a block diagram illustrating the main control system of the medical RF apparatus of FIG. 1.

FIG. 3 is a block diagram illustrating the main control system of the RF treatment apparatus of FIG. 1. Hereinafter, the control structure of the medical RF apparatus according to the present embodiment will be described in more detail, referring to FIG. 3.

The control unit 140 is a configuration that controls various kinds of constituting elements of the main body 100 and the hand piece 200. As illustrated in FIG. 3, the control unit 140 can insert the insertion unit 250 into the tissue, withdraw from the tissue, or control the insertion depth of the insertion unit 250, by controlling the operation of the driving unit 210 of the hand piece. Additionally, the control unit 140 can control on/off operation of an RF pulse and RF pulse parameters by controlling the RF generator 110, whereby the RF treatment apparatus 1 can insert the microneedles inside of the tissue, and then provide RF pulses with appropriate parameters.

In particular, the setting unit 120 is a configuration in which a user can set the details of treatment. Additionally, the control unit 140 controls various configurations to perform a treatment operation based on the details set by the user through the setting unit 120. The setting unit 120 may be comprised of the display unit and/or switch, and it is possible that the setting unit 120 display various options to the user through the display unit 102 and the user select the displayed option.

Additionally, the RF treatment apparatus 1 further includes a memory unit 130 in which various kinds of data are stored. The control unit 140 can store information necessary for controlling the RF treatment apparatus in the memory unit or retrieve the data stored in the memory unit 130 and utilize in the control.

Furthermore, the RF treatment apparatus further include a monitoring unit 260. The monitoring unit 260 is a configuration for monitoring the information on the state of tissue that corresponds to the treatment site during the treatment. The tissue monitoring unit 260 is a configuration for monitoring the temperature of tissue, monitoring the impedance in the pathway for the transmission of RF energy being formed via tissue, and monitoring at least one among the various kinds of information, such as presence of a contact with the hand piece, state under pressure, etc., necessary for treatment.

For example, the monitoring unit 260 of the present embodiment is provided on the pathway where RF energy is transmitted, and is thus configured to monitor the impedance in the pathway where RF energy is transmitted via tissue. The monitoring unit may be provided on the RF transmission path in the hand piece or may possibly be provided on the RF transmission path in the main body. The monitoring unit 260 can monitor the impedance value by applying a separate test current to the insertion unit 250 or can monitor the impedance value being measured during the transmission of RF pulses for treatment. In particular, since the impedance being measured varies depending on the characteristics of a patient, change in tissue state, etc., the impedance may be interpreted as "impedance of tissue" for convenience purposes. In the present invention, the impedance of tissue can be monitored in the monitoring unit 260 before or during the process of treatment, and the details of treatment can be controlled based on the results of the monitoring.

Figure 4:
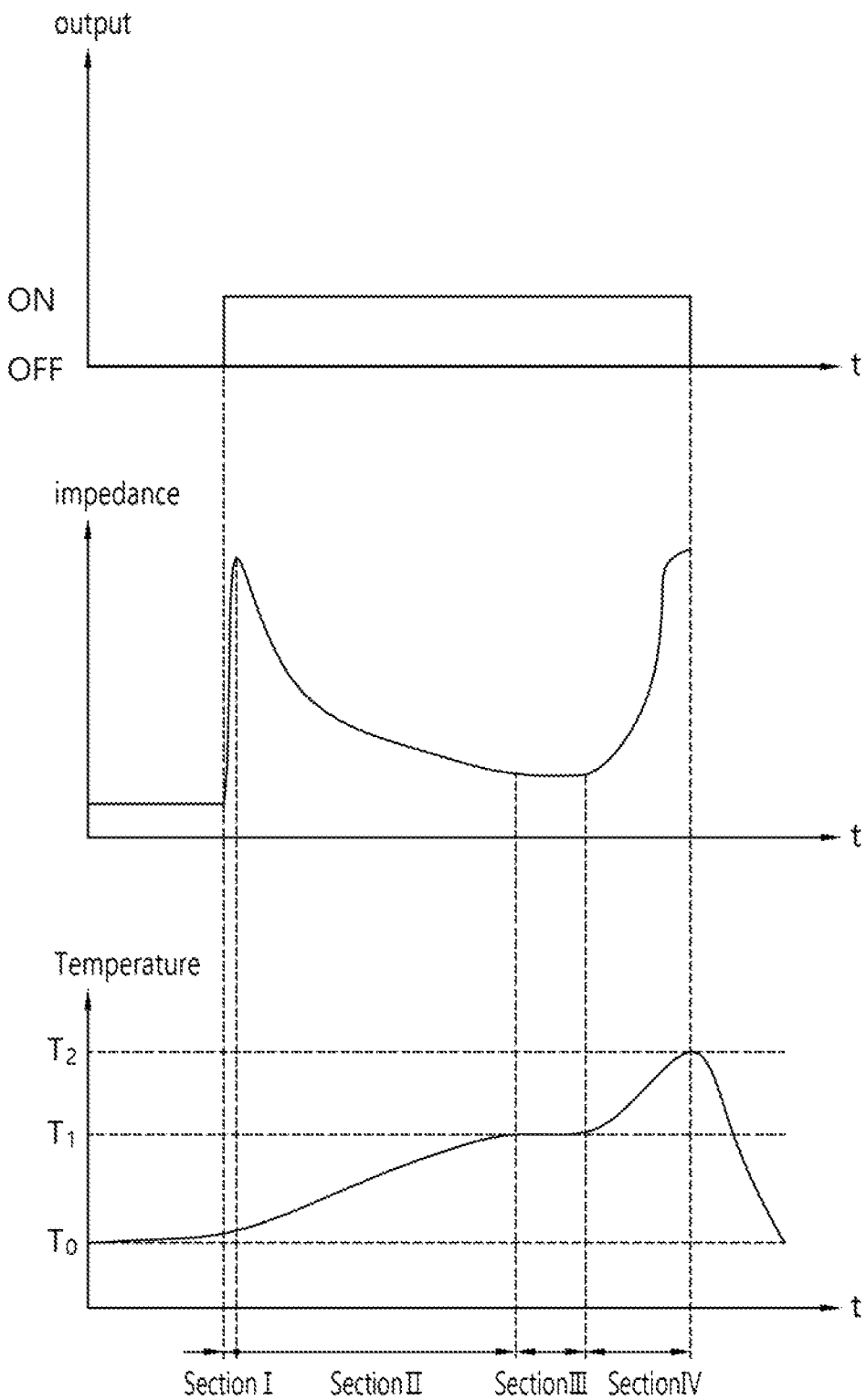
FIG. 4 is a graph illustrating the impedance values of tissue and changes in tissue temperature that appear as an RF pulse is applied during treatment.

FIG. 4 is a graph illustrating impedance values of tissue and changes in tissue temperature that appear as an RF pulse is applied during treatment. In FIG. 4, to provide explanations on how tissue undergoes changes as RF energy is transmitted, the RF pulse was sustained until the time that the tissue temperature rises and thus the tissue becomes desiccated.

As illustrated in FIG. 4, once the RF pulse starts to become applied, the impedance drastically increases while tissue-constituting materials are redisposed and become stabilized as the current is applied (Section I). Additionally, the impedance value becomes slowly decreased as the tissue-constituting materials are stabilized (Section II). During the Sections I and II, there appears a feature that temperature gradually increases from the original temperature (To).

Then, as RF pulses are sustained, as the impedance value of the tissue continuously decreases, there occurs a section that remains almost constant within a predetermined range (Section III). The Section III shows a feature that the impedance of tissue becomes stabilized and the temperature of the tissue is also stabilized in a section of 60° C. to 80° C. (T1). Additionally, as a result of clinical experiments, it is determined that the Section III is a Section where substantial treatment is performed while minimizing the damage of the tissues inside of the skin, such as dermal layer or adipose layer and subcutaneous fat layer, in the corresponding Section.

Then, if the RF pulses are sustained, there occurs a feature that the impedance values of the tissue exceed the predetermined range and increase at a rate of a drastic change (Section IV). In this section, as RF energy is sustained, tissue desiccation that the moisture inside the tissue is almost eliminated is achieved. In particular, as the moisture inside the tissue contributing to electrical conductivity is removed, the impedance value of the tissue rapidly increases, and as a result, the tissue temperature also rapidly increases thus causing tissue damage.

As reviewed above, as RF energy is sustained, the tissue state undergoes changes while going through Sections I to IV, and as a result, effective treatment may be provided or excessive treatment may be provided thus resulting in tissue damage.

Figure 5:
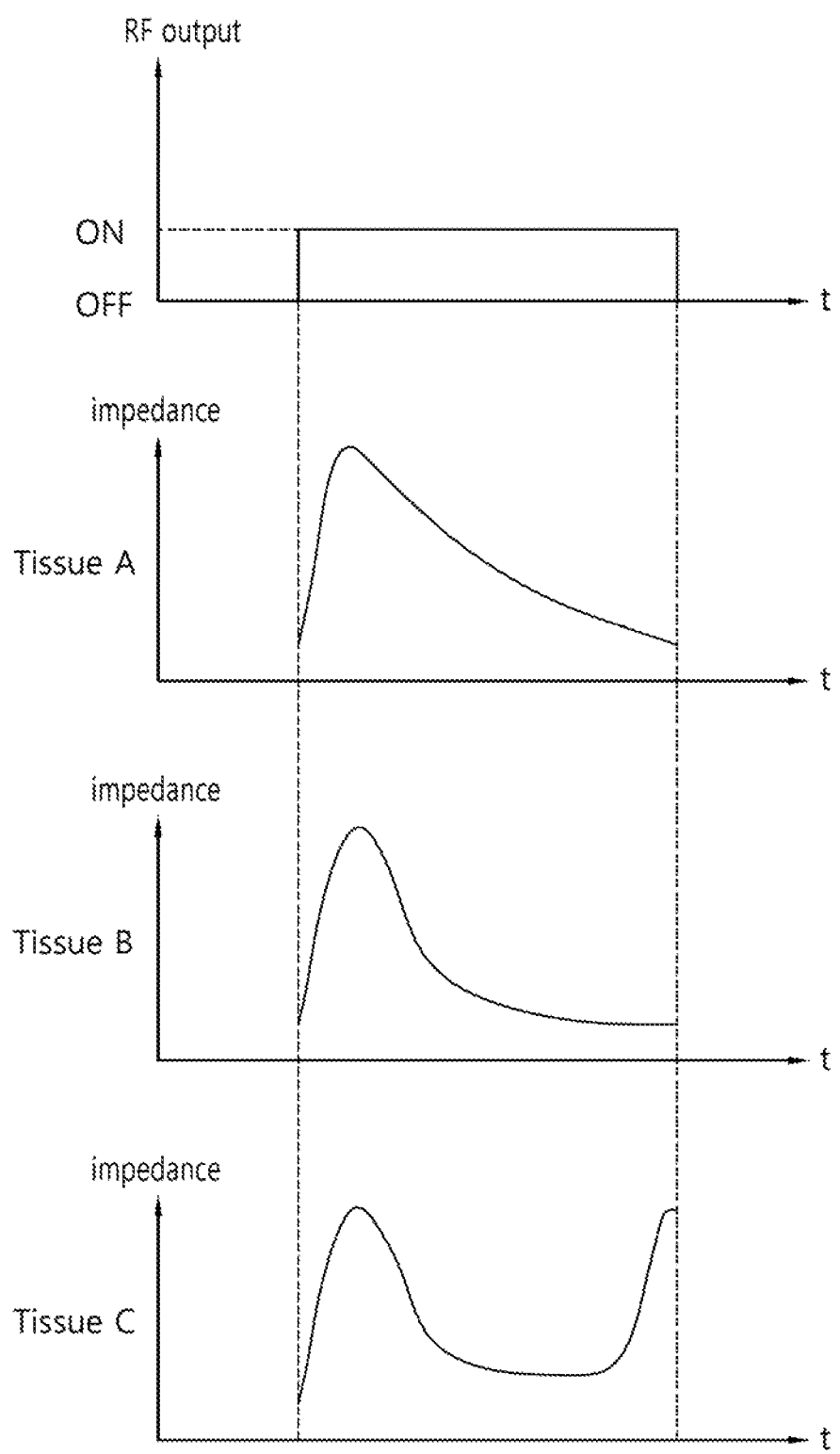
FIG. 5 is a graph illustrating the changes in the state of various tissues by one RF pulse.

FIG. 5 is a graph illustrating changes in state of various tissues by one RF pulse. Specifically, FIG. 5 shows impedance characteristics that appear in three tissues which are different from each other, when RF pulses having the same parameter were irradiated.

First, the impedance characteristics of tissue A exhibited a feature where the pulse duration time was terminated while the initial impedance decreased after a rapid increase. That is, the characteristics exhibit the features corresponding to those of Sections I and II, however, the entry into Section III was not made while RF pulses were being transmitted. Accordingly, in the case of the tissue A, the treatment was terminated in a state that the temperature corresponding to T1 was not reached, and it was thus confirmed that the treatment was not appropriately provided.

In contrast, the impedance characteristics of the tissue B exhibited that the initial impedance drastically increased and then gradually decreased and the impedance value was maintained in a certain Section. That is, during the irradiation of the RF pulse, the entry was progressed into Section III by going through with Sections I and II. Accordingly, in the case of the tissue B, the tissue arrives at the temperature corresponding to T1 and the temperature was maintained for a predetermined time, and thus it can be determined that the treatment was normally proceeded.

Furthermore, the impedance characteristics of the tissue C exhibited a feature that impedance value was drastically increased during the later-half of the delayed time of RF pulse, while exhibiting the impedance characteristics of the tissue B. Accordingly, it can be confirmed that the entry was progressed into Section IV after going through with Sections I to III during the irradiation of RF pulse. Accordingly, in the case of the tissue C, it can be determined that an excess treatment where the tissue temperature was excessively increased and thus the tissue reached the state of desiccation thus resulting in damage of the tissue.

As such, even in the case of transmitting RF with the same parameter, the effects of treatment appear differently depending on the state and characteristics of the tissue. That is, although the treatment is proceeded under the same conditions, the results of the treatment may show differently according to the characteristics such as race, age, body constitution of a patient. Furthermore, even in the same patient, the treatment may show different results according to the state of the body, duration of treatment, etc. Accordingly, the RF treatment apparatus of the present embodiment may be used to perform optimized treatment by monitoring the characteristics of tissue and control the RF pulse parameters based on the results of the monitoring.

In the RF treatment apparatus 1 according to the present invention, the treatment is performed by inserting each insertion unit into a plurality of sites for treatment followed by transmitting an RF pulse thereto. In particular, the control unit 140 can perform monitoring the results of treatment by an RF pulse transmitted at a preceding site and control so that the results of monitoring can be reflected for the treatment of sites to be treated thereafter. Specifically, in the case where treatment is proceeded by transmitting each RF pulse from a $1^{st}$ site, a $2^{nd}$ site, a $3^{rd}$ site to the $n^{th}$ site, a first RF pulse can be transmitted to the $1^{st}$ site and the treatment results are monitored, and a second RF pulse parameter to be transmitted to the $2^{nd}$ site can be controlled based on the results of the monitoring. Additionally, the second RF pulse parameter can be transmitted to the $2^{nd}$ site and the treatment results are monitored, and a third RF pulse parameter to be transmitted to the $3^{rd}$ site can be controlled based on the results of the monitoring. As such, it is possible to proceed with treatment by finding the optimal RF pulse parameters suitable for the characteristics of tissue, based on the treatment results at the adjacent sites that were treated in advance.

There are various methods that the control unit 140 can employ to control the RF pulse parameters based on the results of the treatment at the preceding site. The RF pulse parameters can be variously controlled by varying at least one of various parameters that constitute the RF pulse. However, in the present embodiment, it is configured to control the output of the RF pulse and the pulse duration among various parameters of the RF pulse. In particular, the amount of energy that each RF pulse transmits to the tissue can be maintained at the same level. Accordingly, the output and pulse duration may not be parameters that can be independently controlled but they may be a combination of parameters that are mutually correlated to be controlled (for example, if the output increases, the pulse duration decreases).

Figure 6:
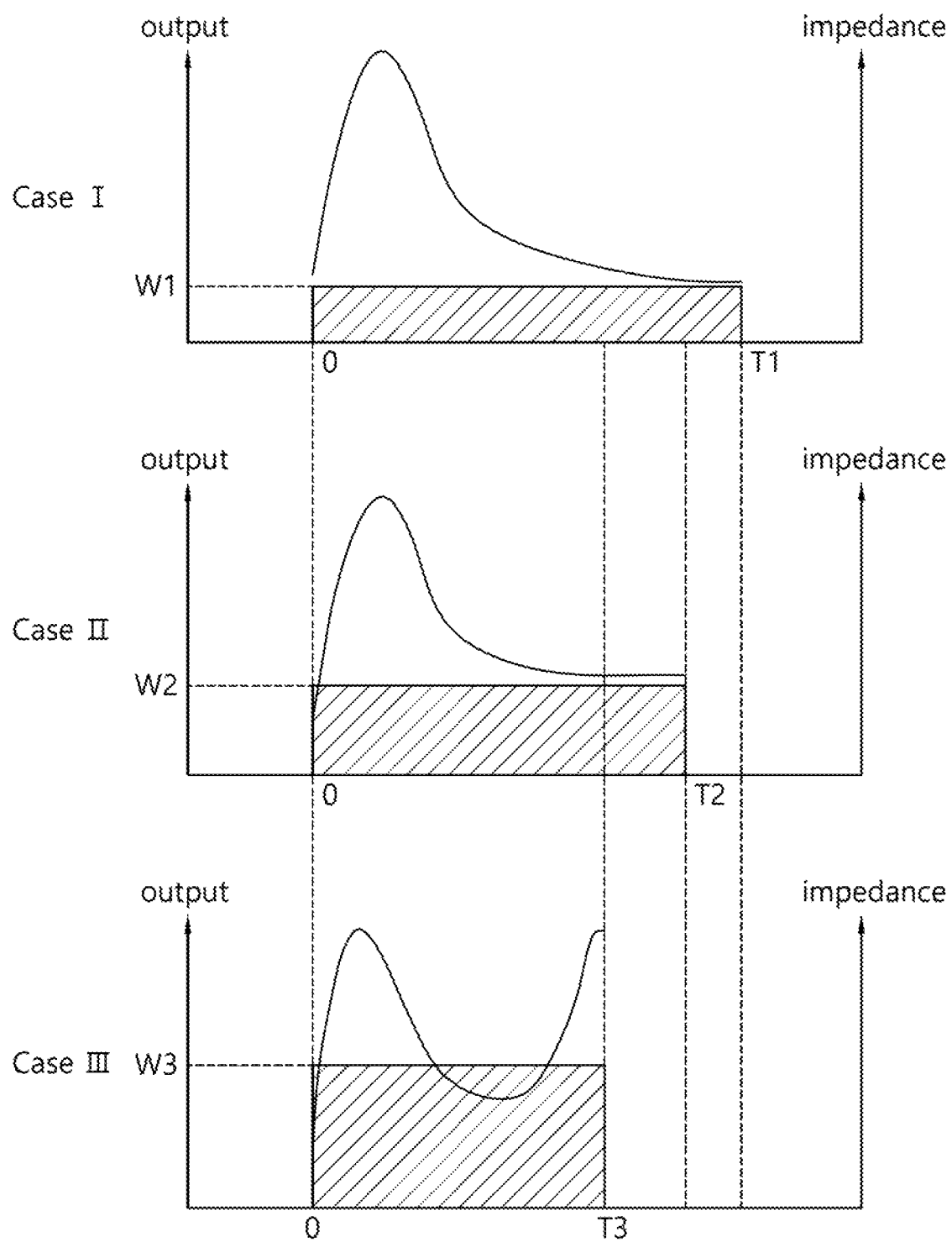
FIG. 6 is a graph illustrating the changes in tissue state according to RF pulse parameters.

FIG. 6 is a graph illustrating the changes in tissue state according to RF pulse parameters. Specifically, FIG. 6 illustrates the changes in tissue impedance when RF pulses with different parameters were transmitted to the same tissue. In particular, the amount of energy that each RF pulse transmits to each tissue is the same (T1×W1, T2×W2, and T3×W3 are all the same), and only the output and pulse duration of each RF pulse are different.

First of all, Case I of FIG. 6 shows a waveform in which the output of the RF pulse is small and the pulse duration of the RF pulse is long; Case II of FIG. 6 shows a waveform in which the output and the pulse duration are relatively in a intermediate level; and FIG. Case IIII of FIG. 6 shows a waveform in which the output of the RF pulse is large and the pulse duration of the RF pulse is short.

In particular, as can be seen from the information on tissue impedance for each waveform, although the RF pulse transmits the same amount of energy to the tissue, the results of tissue treatment may vary depending on the waveform of the RF pulse. As in the case of Case I of FIG. 6 where a small amount of output energy is provided for a relatively long duration, sufficient tissue treatment cannot be provided. In this case, the intensity of treatment can be improved by increasing the output and reducing the duration (see Case II of FIG. 6). Additionally, in the case of Case III of FIG. 6 where a high amount of output energy is provided for a relatively short duration, it may result in excess treatment thereby causing damage on the tissue. In this case, the intensity of treatment can be lowered via control of lowering the output and increasing the duration (see Case II of FIG. 6).

Accordingly, the control unit of the RF treatment apparatus of the present embodiment can control the output and pulse duration of an RF pulse while maintaining the amount of energy being transmitted to the tissue by each RF pulse. Additionally, with these methods of controlling parameters, it is possible to proceed with optimal treatment based on the results monitored at the sites treated earlier. Hereinafter, the details of optimum control of the RF pulse will be explained in more detail with reference to FIG. 3.

Figure 7:
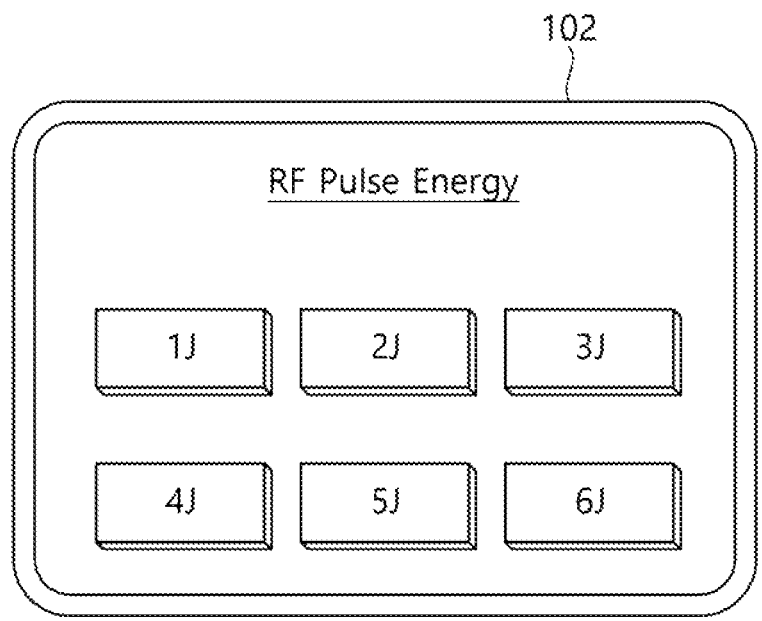
FIG. 7 is a graph illustrating an embodiment of the setting unit of FIG. 3.

First, the setting unit 120 is a configuration that a user can set the details of treatment, which is configured to select the amount of energy of the RF pulse to be applied to the treatment. FIG. 7 is a graph illustrating an embodiment of the setting unit of FIG. 3. As illustrated in FIG. 7, a plurality of options can be indicated to a user through a display unit 102, and the user can select the amount of the RF pulse by selecting the indicated option. Although the amount of RF energy is represented as an option to be indicated in FIG. 7, however, it is also possible to indicate selectable options based on intensity of treatment and lesions.

The setting unit 120 described above is configured such that a user selects only one parameter corresponding to the energy amount of an RF pulse, however, it is also possible that the setting unit 120 is configured to additionally set various parameters (e.g., an output and a pulse duration) in detail. However, if it is configured such that a user can set the parameters in detail, the details of treatment may vary depending on the experiences of the user, and there is also a disadvantage in that the manipulation of the user becomes inconvenience. Accordingly, in the present invention, an optimal treatment can be performed by guiding an appropriate energy amount per RF pulse according to the approximate characteristics (age and race) and lesions for treatment of the patient, and by controlling the specific parameters of the RF pulse through monitoring of impedance within the amount of energy range selected by the user.

Figure 8:
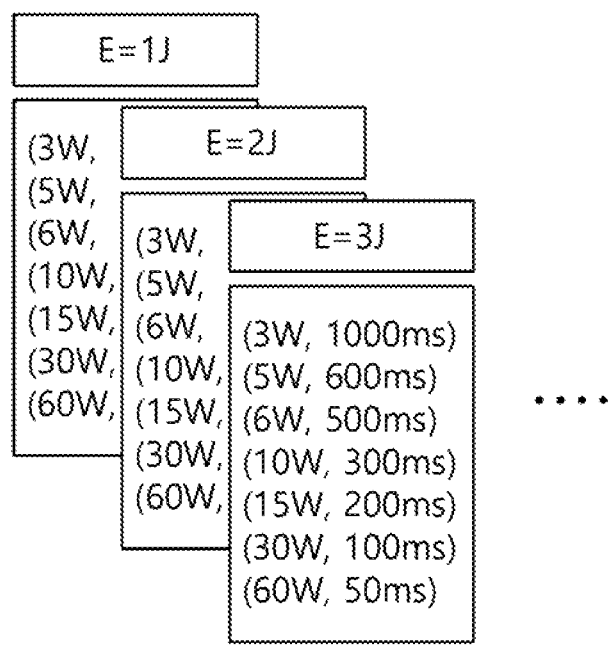
FIG. 8 is a schematic diagram illustrating the contents of data stored in the memory unit of FIG. 3.

FIG. 8 is a schematic diagram illustrating the contents of data stored in the memory unit of FIG. 3. As illustrated in FIG. 8, the memory unit 130 stored data on various combinations of parameters according to the RF pulse energy. In particular, the combinations of RF pulse parameters may be a combination of pulse output and pulse duration. As illustrated in FIG. 8, the memory unit 130 can store a plurality of combinations of RF pulse parameters corresponding to each energy, with respect to the energy being transmitted by RF pulses. In FIG. 8, in an embodiment, combinations of a plurality of parameters corresponding to RF pulses that transmit 3 J of energy are indicated, and additionally, the memory unit 130 can store data relating to combinations of parameters with respect to each energy.

Accordingly, once the user sets the energy amount of an RF pulse to be used through the setting unit 120 during treatment, the control unit 140 selects any one from the combinations of parameters corresponding to the subject energy amount stored in the memory unit 130 and thereby controls the output of the RF pulse. In particular, at least one of the plurality of combinations of RF pulse parameters corresponding to each energy amount may be a combination of parameters having the most appropriate results of treatment under general conditions via clinical experiments. Accordingly, the control unit can be controlled to generate the first RF pulse by the predetermined optimum combination of parameters among the combinations of parameters corresponding to the energy amount set by the user. Additionally, the RF pulse parameters can be controlled by controlling the parameter combinations into an appropriate combination based on the monitoring results of impedance by the first RF pulse thereafter. It is possible that the optimum parameter combination described above is configured to have one combination per energy, but it is also possible that each independent optimum parameter combination may be assigned according to the age, sex, race, etc.

Meanwhile, the monitoring unit 260 monitors the information on tissue impedance while the RF pulses are transmitted, as described above. Additionally, the control unit 140 determines the information on tissues states whether the tissue has been effectively treated based on the monitored information on impedance, whether the tissue has not been appropriately treated, whether the tissue has been excessively treated, etc.

There are various methods that the control unit 140 can employ so as to determine the information on tissue states based on the monitored information on impedance. For example, the information on state can be determined by comparing the patterns of the changes in impedance during the pulse duration of an RF pulse with the reference pattern already stored (for example, when the impedance pattern is similar to that of Case I of FIG. 6, it is determined as insufficient treatment; when the impedance pattern is similar to that of Case II of FIG. 6, it is determined as normal treatment; and when the impedance pattern is similar to that of Case III of FIG. 6, it is determined as excess treatment). However, the control unit of the present embodiment can determine the information on tissue states based on the rate of change in impedance during the duration of the RF pulse, without using an additional reference pattern.

Specifically, after the impedance pattern passes through the initial impedance stabilizing section (Section I), if there is no section in which the impedance is maintained constant within a predetermined range, it is determined that sufficient treatment has not been provided (see Case I of FIG. 6). Additionally, after the impedance pattern passes through the initial impedance stabilizing section, if a Section in which the impedance again drastically increases higher than the predetermined rate of change appears, it is determined that excess treatment has been provided (see Case III of FIG. 6). In contrast, with respect to the impedance pattern, if there is a Section where the impedance value is maintained within the predetermined range but there is no Section where the impedance value drastically increases, it is determined that treatment has been appropriately provided (see Case II of FIG. 6).

As such, the control unit 140 determines the treated state of tissue based on the change in impedance in the tissue while the RF pulse is transmitted. Additionally, based on the same, the control unit 140 controls the RF pulse parameters being transmitted to the subsequent sites. As a result of the determination by the control unit 140, if it is determined that treatment was appropriately provided in the previous treatment, an RF pulse with the same parameter can be transmitted to the subsequent sites. In contrast, if it is determined that treatment was not appropriately provided in the previous treatment, an RF pulse can be controlled by a combination of parameters where the output increases and the pulse duration decreases among the RF pulse parameters and transmitted to the subsequent sites. This is because, as explained in FIG. 6 previously, even in the case of an RF pulse which transmits the same level of energy, when the RF pulse is transmitted by a high output for a short period of time, the tissue temperature can be more effectively increased thereby being capable of improving treatment intensity. Meanwhile, if it is determined that excess treatment has been provided in the previous treatment, an RF pulse can be controlled by a combination of parameters where the output decreases and the pulse duration increases among the RF pulse parameters and transmitted to the subsequent sites.

As such, the RF treatment apparatus 1 according to the present invention can control the RF pulse parameters in a real-time manner based on the results of the previous treatment, and thus it is possible that the RF treatment apparatus 1 can provide an appropriate RF pulse by continuously monitoring the tissue characteristics of a patient, and furthermore, the tissue characteristics according to the sites.

Figure 9:
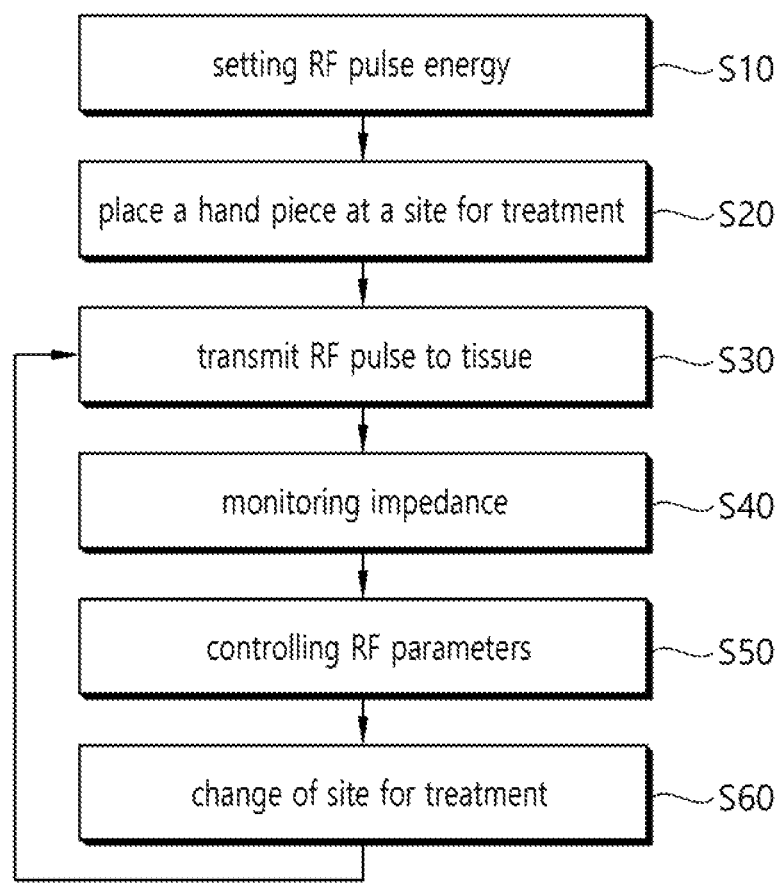
FIG. 9 is a flow chart illustrating the method of controlling the medical RF apparatus of FIG. 1.

FIG. 9 is a flow chart illustrating the method of controlling the medical RF apparatus of FIG. 1. Hereinafter, a control method of an RF treatment apparatus according to the present embodiment will be described in detail with reference to FIG. 9.

Before proceeding with the treatment, a user performs a step of setting the treatment details through the setting unit 120 (S10). Through this step, various information can be inputted and the details of the treatment can be set.

As one of them, the energy amount of the RF pulse used in the treatment can be set. As a result, the RF pulse to be transmitted during treatment can maintain the energy to be transmitted to the tissue through a single pulse at the same level even when the parameters are changed by the control unit 140. For example, when a user selects 3 J as the RF pulse energy, control unit 140 can maintain the energy of the RF pulse at the same level by controlling the RF pulse by selecting among the combinations of RF pulse parameters corresponding to 3 J stored in the memory unit 130 (see FIG. 8).

Meanwhile, once the set-up step is accomplished, a user can place the hand piece 200 in the site for treatment to perform treatment (S20). The treatment using the RF treatment apparatus according to the present invention can be proceeded in such a manner that the RF energy is transmitted by inserting the insertion unit 250 at a plurality of sites for treatment, and can place the hand piece at a first site as the first site for treatment.

When the hand piece 200 is positioned at the first site, a step of treating the site is performed. The present step is proceeded in such a manner that after inserting the insertion unit 250 into the inside of the tissue in the first site, an RF generator 110 is driven and thereby a first RF pulse is transmitted (S30). In particular, the first RF pulse being transmitted to the first site can be controlled to have a combination of parameters predetermined as the optimum combination among the combinations of RF parameters stored in the memory unit 130. In an embodiment, since the energy selected by the user in the previous step described above is 3 J, the control unit 140 can generate RF pulses with parameters stored as the optimum combination where the output is 10 W and the pulse duration is 300 ms, among the combination of parameters corresponding to 3 J stored in the memory unit 130, and thereby perform the treatment.

In particular, a monitoring unit 260 performs monitoring of the changes in tissue impedance while the RF pulse is transmitted (S40). Additionally, the control unit 140 confirms whether the treatment has been appropriately provided by determining the change in tissue state based on the same, and performs the step of controlling the RF pulse parameters being irradiated to the following site based on the results of the determination (S50).

FIG. 9 illustrates that the step of transmitting an RF pulse (S30) and the step of monitoring the impedance (S40) as separate steps, however, this classification was for the convenience purposes, and it is possible to perform these two steps simultaneously. That is, the impedance value of tissue can be monitored by monitoring the information on the impedance of a circuit that passes through with the tissue while the RF pulse is applied into the tissue. Additionally, the step of monitoring the impedance (S40) and the step of controlling the RF parameters are illustrated as separated steps. However, these two steps are also classified for the convenience purposes, and it is possible to perform these two steps simultaneously or alternatively.

Figure 10:
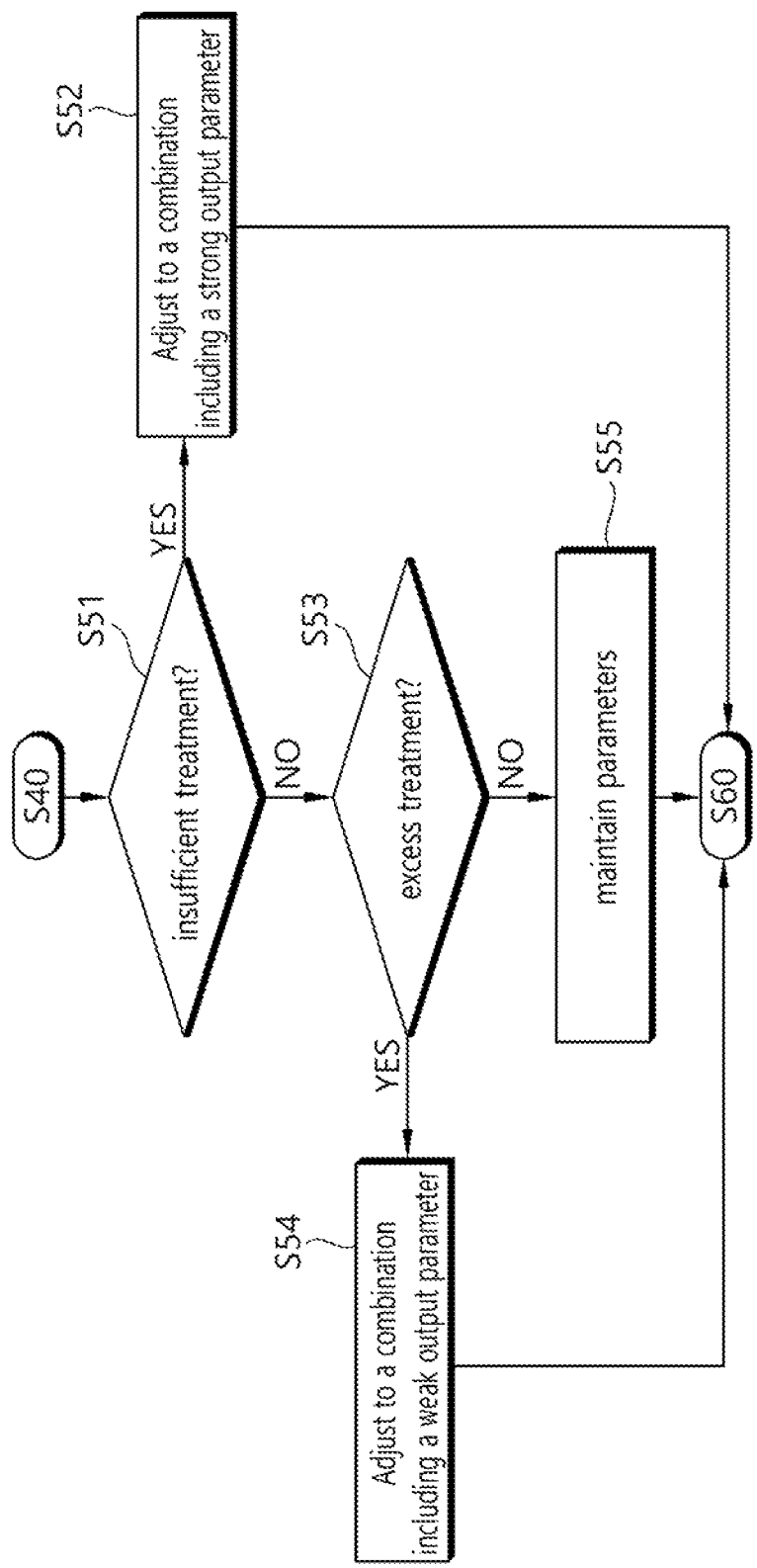
FIG. 10 is a flow chart more specifically illustrating the steps of controlling RF parameters of FIG. 9.

FIG. 10 is a flowchart which more specifically illustrates the step of controlling the RF parameters of FIG. 9. Hereinafter, the step of controlling the RF parameters will be described in more detail with reference to FIG. 10.

First, the control unit 140 determines whether the treatment has been properly performed based on the monitored information on impedance. First, the monitored impedance values are analyzed and it is determined whether the treatment was properly performed in the first site (S51). The determination on whether the treatment was sufficient or not can be made based on the presence/absence of a Section where the impedance values are maintained constantly within the predetermined range after the Section of the initial impedance stabilization. From the foregoing, if it is determined that there is no Section where the impedance values are maintained constantly, the control unit 140 performs a step of controlling the RF pulse parameters so that the treatment can be effectively provided in the subsequent sites (S52). The present step can be controlled by a combination where the output value is greater than the first RF pulse parameter and the pulse duration is shorter, among the combinations of parameters stored in the memory unit (i.e., among the combination of parameters corresponding to the predetermined energy). For example, in the case where the output of the first RF pulse is 10 W and the pulse duration is 300 ms, it is possible to control the second pulse through the present step by a combination of parameters where the output is 15 W and the pulse duration is 200 ms.

As a result of the analysis of the impedance values, if it is determined that the treatment at the first site was not insufficient, it is to be determined whether excess treatment has been provided to the contrary (S53). The determination on whether excess treatment has been provided can be made based on the presence/absence of a Section where the impedance again drastically increases over the predetermined rate of change, after passing the initial impedance stabilized Section. From the foregoing, if it is determined that there is a Section where the impedance value drastically increases higher than the predetermined rate of change at the later-half of the pulse duration, it is determined that excess treatment has been provided. Accordingly, the control unit performs a step of controlling RF pulse parameters so that excess treatment can be avoided in the subsequent sites (S54). In the present step, the control can be made by a combination in which the output value is lower compared to the first pulse parameter and the pulse duration is longer, among the combination of parameters stored in the memory unit. For example, in the case where the output is 10 W and the pulse duration is 300 ms for the first RF pulse, it is possible to control the second pulse by a combination of parameters where the output is 6 W and the pulse duration is 500 ms.

However, as a result of the analysis of the treated state with regard to the first site, if it is determined that the normal treatment was provided without being insufficient or excessive treatment, the control unit 140 can control so that the treatment in the following site can be proceeded while maintaining the RF pulse parameters (S55).

The parameters of the second pulse transmitted to the subsequent second site are controlled by reflecting the treatment result at the first site through the steps described above (S50). Additionally, after changing the site for treatment to the second site (S60), a step of transmitting a second RF pulse inside of the tissue at the second site can be performed using the controlled RF pulse parameters (S30). Additionally, as is the case with the steps described above, the impedance can be monitored at the second site while the second RF pulse is transmitted, a step of additionally controlling/maintaining the second RF pulse parameters is performed based on the same, and then the above steps can be repeatedly performed after changing the treatment site to a third site.

As such, once a user selects the energy parameters, the RF treatment apparatus according to the present invention can transmit an RF pulse with appropriate parameters by determining the treated state according to the characteristics through the impedance monitoring.

In particular, since RF parameters are controlled based on the treatment results at previous treatment sites, a customized control suitable for the characteristics of a patient and tissues thereof can be performed. Additionally, there is an advantage in that treatment can be performed by reflecting the characteristics of tissues that may vary from site to site even in the case of the same tissue.

Furthermore, the present invention has advantages in that the differences in treatment results by a user's experiences can be minimized, and optimal treatment can be proceeded by performing a control for compensating various conditions such as race, age, conditions of a patient, etc., by the apparatus itself.

Hereinafter, a medical RF apparatus according to a second embodiment of the present invention will be described with reference to drawings. The medical RF apparatus according to the second embodiment is comprised of a tissue testing apparatus using RF pulses (hereinafter, an RF testing apparatus). While the RF treatment apparatus described in previous embodiments is an apparatus for treating tissue lesions using RF pulses, the RF testing apparatus 1200 according to the present embodiment is an apparatus for measuring tissue characteristics using RF pulses and thus the uses of these apparatuses are different from each other. However, considering that the RF testing apparatus also measures tissue characteristics by transmitting RF pulses to tissues followed by monitoring the states of these tissues, the RF testing apparatus can be configured to include constituting elements similar to those of the RF treatment apparatus according to the embodiments described above. In particular, the RF testing apparatus 1200 according to the present embodiment may be configured to include constituting elements similar to those of the RF testing apparatus described above, excluding part of the constitutions relating to control and calculation systems. Accordingly, in providing explanations on the RF testing apparatus according to the present embodiment, the constituting elements similar to those in previous embodiments described above are denoted by the same names, however, with regard to the common technical features shared between them, detailed descriptions thereto will be replaced by the explanations in the embodiments described above so as to avoid duplication of descriptions. However, it should be understood that the embodiment described below is merely one embodiment of the RF testing apparatus, and that the present invention is not limited to the embodiment described below and various modifications may be made thereto.

The RF testing apparatus 1200 according to the present embodiment is configured to include a main body 1100, a hand piece 1200, and a connection unit 1300 which connects between the main body and the hand piece (FIGS. 1 and 2). Additionally, an RF generator 1110 is provided inside of the main body and a switch 1101 and a display unit 1102 are provided on the external surface of the main body and thereby the operation of the testing apparatus can be controlled or various information can be indicated to a user.

Additionally, the hand piece 1200 measures the characteristics of a subject tissue at a position adjacent to the tissue to be examined. The hand piece 1200 according to the present embodiment is configured to include an insertion unit 1250, a driving unit 1210, and a manipulation unit 1220 for manipulating the insertion unit and the driving unit, as is the case with the embodiment described above. The insertion unit 1250 is configured to have a tip module structure including microneedles as illustrated in FIGS. 1 and 2, and it is connected to an RF generator and transmits a test pulse used in the examination of tissue characteristics. Additionally, the driving unit 1210 moves the insertion unit 1250 back and forth so that the insertion unit 1250 can be inserted inside of the tissue for its examination.

However, the specific details with regard to the mechanical structure, driving modes, and RF energy transmission system of the main body and the hand piece are similar to the RF treatment apparatus in embodiments described above and thus the specific explanations are omitted herein.

Figure 11:
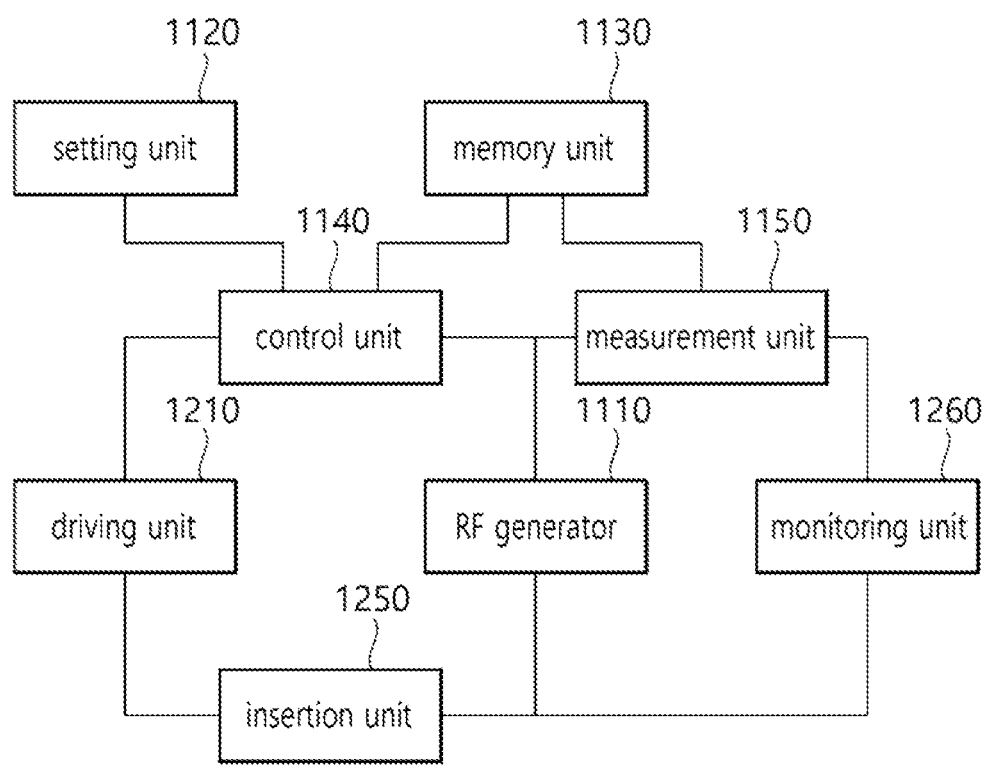
FIG. 11 is a block diagram illustrating the main control system of the medical RF apparatus according to a second embodiment.

FIG. 11 is a block diagram illustrating the main control system of the RF test apparatus according to a second embodiment. Hereinafter, a control structure of the RF testing apparatus according to the present embodiment will be described with reference to drawings.

The control unit 1140 is a constitution that controls the movement of various constituting elements of the main body and the hand piece as is the case with the embodiments described above. Accordingly, the control unit 1140 can control the movement of the driving unit 1210 and thereby selectively insert the insertion unit 1250 into the inside of tissue, and control the RF generator 1110 and thereby control the on/off movement of RF pulses being transmitted at the time of examination and test RF pulse parameters.

The setting unit 1120 is a constitution by which a user can set the details of examination. The user can set examination patterns, examination recovery, etc. through the setting unit 1120, and the control unit 1140 can control various constituting elements so as to perform examination movement based on the set details. Various kinds of data to be used for the examination are stored in the memory unit 1130. Accordingly, the control unit 1140 can store necessary information in the memory unit 1130 or retrieve the data stored in the memory unit 1130 and utilize them for the control.

Additionally, a monitoring unit 1260 is a constitution for monitoring the information on the state of tissue while the examination of the characteristics of the tissue is proceeded. As is the case with the embodiments described above, the monitoring unit 1260 can monitor the changes in tissue impedance, monitor the changes in tissue temperature, or monitor other parameters.

Additionally, the measurement unit 1150 is a constitution which determines the tissue characteristics of a patients based on the values monitored in the monitoring unit 1260. FIG. 11 illustrates that the measurement unit 1150 is a separate constitution which is distinguished from a control unit or a monitoring unit. However, it is possible that the measurement unit 1150 is provided as a lower-level constituting element of the control unit or as a lower-level constituting element of the monitoring unit.

Previously, as explained in FIG. 4, the state of tissue sequentially undergoes changes from Section I to Section IV while an RF pulse is applied to the tissue of a patient. In particular, in Section IV, there occurs a phenomenon that the impedance of the tissue drastically increases as the tissue desiccation occurs and the temperature of the tissue drastically increases.

Here, an experiment was performed on skin tissues of a plurality of patient group, and as a result, it was confirmed that even when RF pulses with the same output are transmitted to the skin tissue, the time point that the pulses enter the Section IV were different from each other. In particular, as the age of the patient became lower it required more time to reach the Section IV. Additionally, even in a similar age group, as the skin tissue was in a better state, it required a longer time to reach the Section IV. This tendency is due to the water-containing characteristics of the tissue, and it is interpreted that as the tissue contains a higher water content it requires a longer time that the tissue becomes desiccated by an RF pulse. Generally, considering that the representative characteristics of tissue aging is dehydration, it can be determined that as the skin has progressed further in terms of senescence, the tissue desiccation occurs within a short period of time under the same conditions. Accordingly, the RF testing apparatus according to the present embodiment can measure the characteristics of tissue based on the changes in tissue by RF pulses.

Again, the constitution of the present embodiment is explained in details with reference to FIG. 11. The control unit 1140 of the present embodiment can insert the insertion unit 1250 into the inside of the tissue to be examined by the operation of the driving unit 1210, and can control to generate a test pulse to be transmitted to the tissue during the examination by operating the RF generator 1110. Here, the test pulse is an RF pulse to be transmitted during the examination and causes the change in the state of the tissue. While the test pulse is transmitted inside of the tissue, the monitoring unit 1260 monitors the changes in the state of the tissue. Additionally, the measurement unit 1150 can determine the characteristics of the tissue by measuring the time required for the desired change in the state of the tissue (tissue desiccation) based on the values detected in the monitoring unit.

Figure 12A:
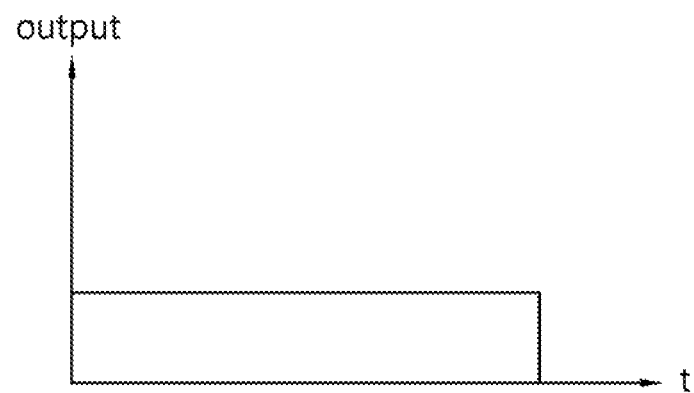
FIGS. 12A and 12B show graphs illustrating the types of output patterns of a test pulse, FIG. 13 show graphs monitoring the changes in tissues of a plurality of patients during an examination.
Figure 12B:
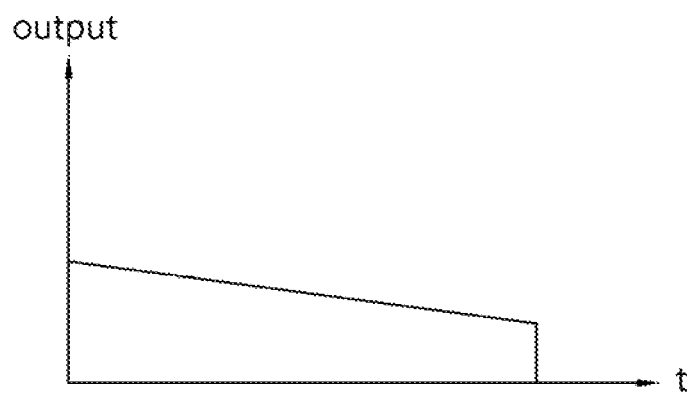

FIG. 12A and FIG. 12B show graphs illustrating the types of output patterns of a test pulse. The output patterns of a test pulse may be configured to have an output with a constant size while the examination is proceeded, as illustrated in FIG. 12A. Alternatively, the output patterns of a test pulse may be configured such that it has a relatively large output at the initial stage of the test pulse and the output gradually decreases as the pulse duration lapses, as illustrated in FIG. 12B. In the output pattern as in FIG. 12B, since the energy amount being transmitted at the time point where the desired change in the tissue occurs is relatively small, it is possible to elucidate the difference in the time point of changes in state although it is a small difference in tissue characteristics, compared to that of FIG. 12A, it is possible to more precisely measure tissue characteristics.

Additionally, the RF testing apparatus 1001 according to the present embodiment may be configured so that various examination modes can be performed according to the race or age of a patient. Here, the output of a test pulse according to each mode is configured differently so that the tissue characteristics in the corresponding race or age can be measured in specific details to be graded (for example, in the case of a mode with respect to white people where skin aging proceeds rapidly, the output size of a test pulse is set to be relatively small, whereas in the case of a mode with respect to Asian people where skin aging proceeds slowly, the output size of a test pulse is set to be relatively large). Accordingly, the user can select an examination mode that corresponds to a patient among a plurality of examination modes through the setting unit 1120 and thereby perform the examination.

Meanwhile, the monitoring unit 1260 is a constitution that monitors the changes in the state of tissue, and in the present embodiment, the monitoring unit 1260 may be configured to measure impedance of tissue while a test pulse is transmitted to the tissue similarly as in the embodiments described above. Accordingly, the monitoring unit 1260 can determine that a desired change has occurred if, after the stabilization of impedance in the Section I, the tissue impedance increases at a rate higher than the predetermined rate of change or increases above the predetermined reference value. However, the configuration of the monitoring unit 1260 is not limited to a constitution for measuring the impedance of tissue, and it is also possible to alter the mode into one that can measure various parameters associated with water content of the tissue. For example, the monitoring unit is comprised of a temperature sensor provided at an end portion of the hand piece, and thus, if the tissue temperature increases above the predetermined temperature, it can be determined that the desired change in state has occurred.

Here, it is possible that the pulse duration of a test pulse is configured to have a constant value. However, in order to prevent unnecessary damage of the tissue, if it is determined that a change in tissue state has occurred, the control unit 1140 can control the RF generator 1110 and thereby terminate the transmission of the test pulse. Accordingly, the pulse duration according to the present embodiment means the time that the tissue reaches the desired change by the test pulse, and the pulse duration can be configured differently according to the tissue to be examined.

The measurement unit 1150 determines tissue characteristics based on the time that the tissue reaches the desired change while the test pulse is transmitted (hereinafter, required time). Here, the time point that calculates the time required may be the time point when the test pulse is applied, and the termination point may be the time point when it is monitored that the tissue has reached the desired change. The measurement unit 1150 can grade tissue characteristics by comparing with the reference data stored in the memory unit 1130. The mode of grading may be achieved by various methods. For example, the health state of tissue may be scored, or the age of the tissue may be calculated by comparing with the data of characteristics with regard to the water content of the tissue according to age, etc. Additionally, it may be configured that the results graded in the measurement unit 1150 are indicated through the display unit so that a user can confirm the examination results.

Figure 13:
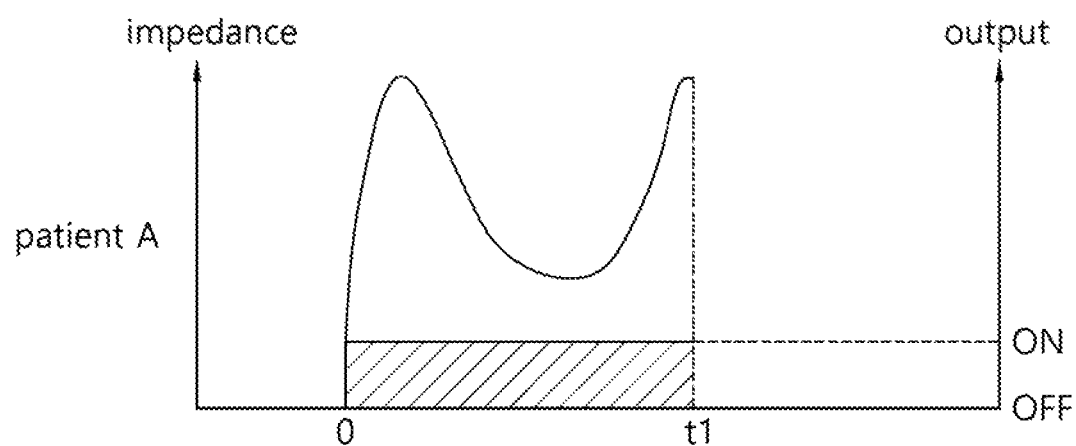
Figure 13:
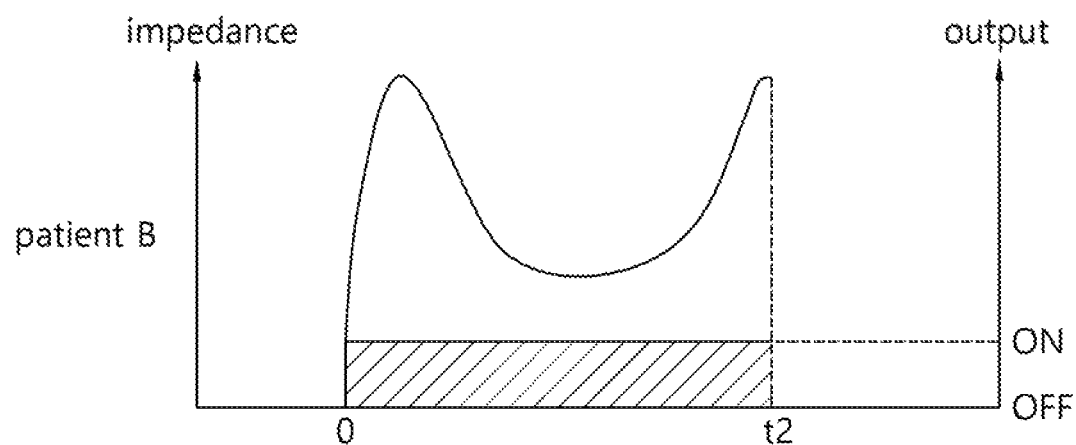
Figure 13:
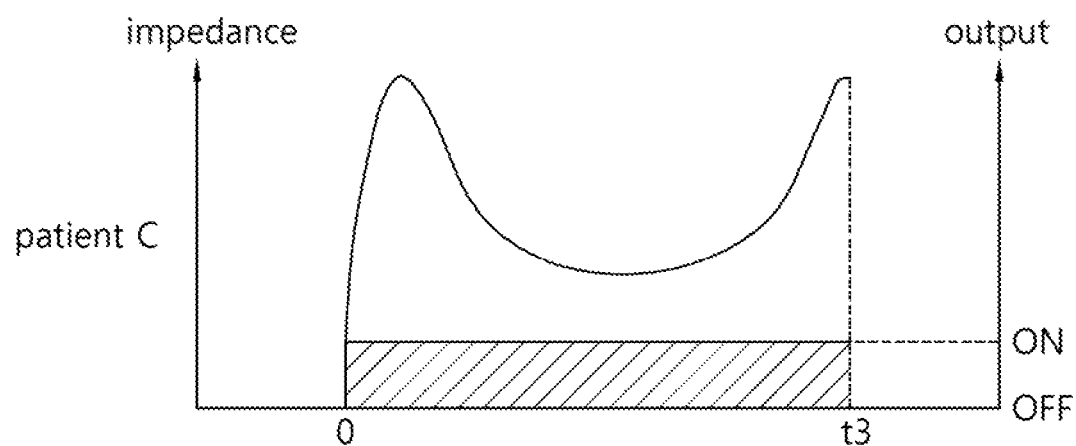

FIG. 13 show graphs illustrating the results of monitoring the changes in tissues of a plurality of patients as the test pulse is applied. As illustrated in FIG. 13, a test pulse having the output of the same parameter (e.g., 10 W) may be transmitted to the same lesion of a plurality of patients and thereby the changes in tissues can be monitored.

In patient A, the desiccation of the tissue to be examined occurred after the lapse of the time t1 following the application of a test pulse; in patient B, the desiccation of the tissue to be examined occurred after the lapse of the time t2 following the application of a test pulse; and in patient C, the desiccation of the tissue to be examined occurred after the lapse of the time t3 following the application of a test pulse (t1<t2<t3).

That is, as a result of the examination, the patient A in which the tissue desiccation has occurred within the shortest period of time showed a low water content in the skin and thus it may be determined that the tissue aging has been most advanced, and the patient C in which the tissue desiccation has occurred within the longest period of time showed a high water content in the skin and thus it may be determined that the tissue aging has been least advanced.

As such, it is possible that the RF testing apparatus 1001 according to the present embodiment can examine the characteristics of tissue using a test pulse that is applied to the tissue. This examination can determine the characteristics of tissue as a result of one measurement for one patient. However, it is also possible that the configuration is made such that a user sets the number of measurements through a setting unit and performs the examination over a plurality of times at each different site, and determines the characteristics of the tissue based on the results of a plurality of examinations.

Figure 14:
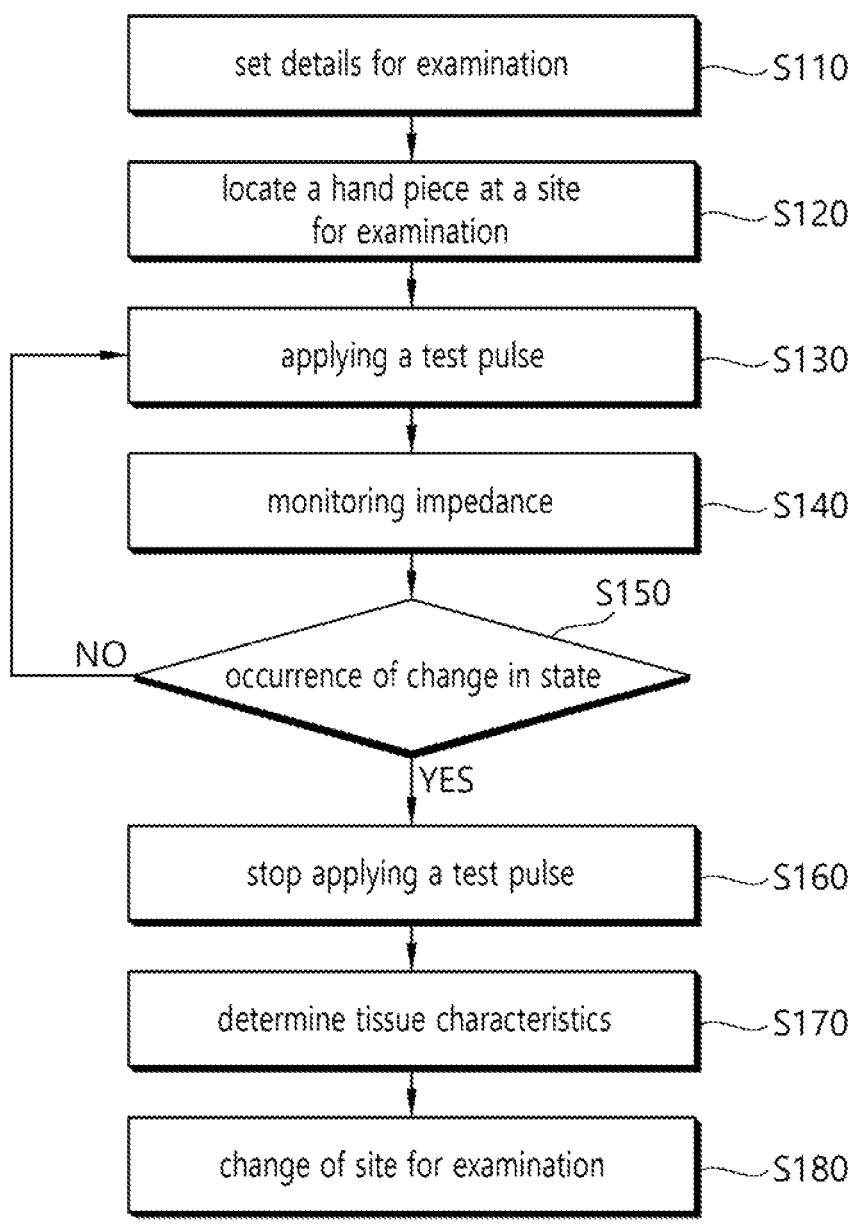
FIG. 14 is a flow chart illustrating the method of controlling the medical RF apparatus of FIG. 11.

FIG. 14 is a flow chart illustrating the method of controlling the medical RF apparatus of FIG. 11. Hereinafter, the method of controlling the examination apparatus according to the present embodiment will be explained in detail.

Before proceeding with the examination, the user proceeds to a step of setting the details of the examination through the setting unit 1120 (S110). Through this step, the user can set the parameters of the test pulse or set the number of examinations, etc. in consideration of the characteristics of the patient.

When the setting step is achieved, the user can place the hand piece 1200 on the surface of tissue to be examined (S120). The examination method according to the present embodiment can be performed by inserting the insertion unit at a plurality of sites of the subject tissue to be examined, and the hand piece 1200 may be placed on the first site for examination as the first site for examination.

Once the hand piece is placed on the first site for examination, the control unit 1140 drives the driving unit 1210 by the user's manipulation and thereby inserts the insertion unit 1250 into the inside of tissue. Additionally, the control unit 1140 drives an RF generator 1110 and thereby transmits a first test pulse (S130). By the same, RF energy is transmitted to the inside of the subject tissue to be examined.

Here, the monitoring unit 1260 monitors the impedance change in tissue while a test pulse is transmitted (S140). Additionally, the monitoring unit 1260 determines the change in the desired state of the tissue (i.e., the presence of occurrence of tissue desiccation) based on the impedance values being monitored (S150). In particular, the presence of occurrence of the desired state can be determined by whether, after the initial impedance stabilization, the impedance values being monitored increases at a rate greater than the predetermined rate of increase or increases greater than the predetermined reference value.

By the same, when the desired change in state did not occur, the state to apply the first test pulse is maintained. However, if it is determined that the desired change in state occurred, the control unit 1140 stops the test pulse being applied to the first site for examination and withdraws the insertion unit 1250 from the tissue by controlling the driving unit 1210.

FIG. 14 illustrates that a step of applying the test pulse (S130), a step of monitoring the impedance (S140), and a step of determining the presence of change in state (S150) are sequentially achieved as separate steps. However, these steps are divided for the convenience purposes and they can be performed simultaneously in parallel with each other in each constituting element during the examination of tissue characteristics.

Once the time required for the occurrence of the desired change in state in the first site for examination is measured through the steps described above, the measurement unit 1150 compares the result with the reference data stored and determines the characteristics of the tissue (S170). In particular, it can be determined that as the time required to reach the desired change becomes longer the state of the tissue is in a better state.

Once the examination on the characteristics of the tissue at the first site is completed, the site for examination is changed to the second site (S180), and the examination on the second site is performed. Additionally, by repeating the above process, the examination on tissue characteristics on a plurality of sites for examination can be performed. Although FIG. 9 illustrates that a step of determining tissue characteristics per site (S170) is performed, in a case where the examination on tissue characteristics on a plurality of sites for examination is to be performed, it is possible that the configuration is made such that the general tissue characteristics of a patient is determined after the application of the test pulse and monitoring of impedance on the plurality of sites are performed.

Figure 15:
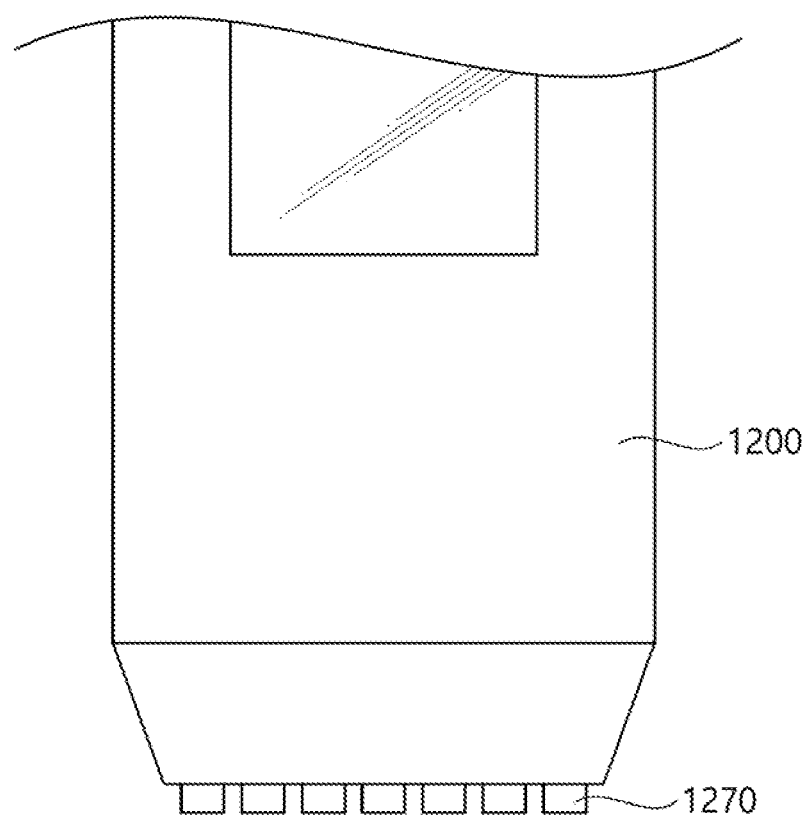
FIG. 15 is a front view illustrating an end portion of a hand piece of the medical RF apparatus according to a third embodiment.

FIG. 15 is a front view illustrating an end portion of a hand piece of the RF testing apparatus according to a third embodiment of the present invention. Hereinafter, the medical RF apparatus according to a third embodiment of the present invention is explained with reference to FIG. 15.

The medical RF apparatus according to the present embodiment is comprised of an RF testing apparatus. However, while the RF testing apparatus of the second embodiment described above is a constitution in which the characteristics of tissue are measured by applying a test current in a state where an insertion unit corresponding to an electrode is inserted into the inside of the tissue, the RF testing apparatus according to the present embodiment is configured such that the characteristics of tissue are measured by applying a test current in a state where an electrode is in contact with the surface of the subject tissue to be examined. Since the inside of the tissue is less affected by the surrounding environment such as humidity compared to the surface of the tissue, the method of invasive examination as in the second embodiment can provide more accurate results. However, the present invention is not limited thereto and it is possible that the RF testing apparatus is configured to perform the examination as in the present embodiment, in consideration of the conveniences of examination and pain of patients.

In this case, compared to the RF testing apparatus according to the second embodiment, the hand piece is not provided with additional insertion unit and driving unit but instead is provided with an electrode unit 1270, which comes into contact with the surface of the tissue, at an end portion of the hand piece 1200. Additionally, the characteristics of tissue can be examined by applying a test pulse on the surface of the tissue through the electrode unit 1270 followed by monitoring the change in impedance on the surface of the tissue.

Hereinafter, the medical RF apparatus according to a fourth embodiment of the present invention is explained with reference to FIG. 16.

In the first and second embodiments described above, embodiments where an RF treatment apparatus and an RF testing apparatus are configured as separate apparatus, respectively. However, as explained above, the constituting elements of the RF treatment apparatus and the 2 RF testing apparatus are similar to each other, and thus the medical RF apparatus according to the present embodiment can be configured such that the RF treatment apparatus and the RF testing apparatus are prepared as one apparatus thereby being capable of performing both examination and treatment.

Specifically, the RF treatment apparatus according to the present embodiment (the apparatus of the present embodiment is an apparatus which can perform both examination and treatment, however, the apparatus can be used to perform an examination as a preliminary step of treatment) can be configured to have a structure corresponding to the RF testing apparatus of the second embodiment described above (see FIGS. 1, 2, and 11). Additionally, the RF treatment apparatus is configured so that a user can select a mode for examination and a mode for treatment through a setting unit 1120. Accordingly, in a case where a user selects a mode for treatment through the setting unit 1120, the major constituting elements such as a setting unit 1120, a memory unit 1130, a control unit 1140, an RF generator 1110, an insertion unit 1250, a driving unit 1210, a monitoring unit 1260, etc., can be configured so that these constituting elements can operate as explained in the first embodiment. Additionally, in a case where a user selects a mode for examination through the setting unit 1120, it is possible that each major constituting element is configured to operate as explained in the second embodiment. However, the structures and details of the operation of each constituting element are explained in detail in the first and second embodiments, and thus, the specific explanations on these constituting elements will be replaced with previous descriptions to avoid repetitive explanations.

Figure 16:
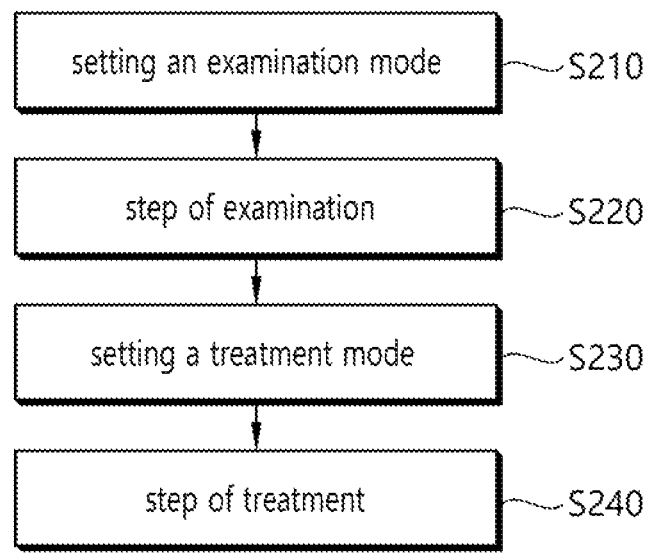
FIG. 16 is a flow chart illustrating an embodiment of the method of controlling the medical RF apparatus according to a fourth embodiment.

FIG. 16 is a flow chart illustrating an embodiment of the method of controlling the RF treatment apparatus according to a fourth embodiment. By the present embodiment, it is possible to perform an examination on tissue characteristics using one apparatus, and it is also possible to perform treatment on tissue lesions. Preferably, as illustrated in FIG. 16, the RF treatment apparatus can be used such that the characteristics of tissue is examined as a preliminary step of treatment and the lesions on tissue are treated based on the results of the tissue characteristics.

In this case, a user first selects a mode for examination through the setting unit (S210). Additionally, the user performs a step of examining the characteristics of tissue using the RF treatment apparatus (S220). In particular, the step of examining the characteristics of tissue may be performed through steps of S110 to S180 of FIG. 11. Once the examination is completed through these steps, the user selects a mode for treatment through the setting unit (S230). Additionally, the user performs a step of treating lesions in tissue using the RF treatment apparatus (S240). In particular, the step of treating lesions in tissue may be performed through steps of S10 to S60 of FIG. 9. Here, the explanations on steps illustrated in FIGS. 9 to 11 are replaced with the explanations of the first and second embodiments provided above.

By performing as described above, as the examination on tissue characteristics is performed as a preliminary step of tissue treatment, the measured results of tissue characteristics can be reflected in tissue treatment for controlling purpose. For example, as explained above, the RF pulse parameters being transmitted to the first site at the time of treatment are determined by an optimum combination of parameters among the parameters for treatment stored in the memory unit 1130. In particular, the optimum combination of parameters may be different according to tissue characteristics (for example, an optimum combination of parameters for tissue with a high water content is [30 W, 100 ms] and an optimum combination of parameters for tissue with a low water content is [10 W, 300 ms]). Accordingly, the control unit 1140 can perform the treatment by controlling parameters of the RF pulse of the first treatment (i.e., the RF pulse for the treatment at the first site) with the optimum combination of parameters corresponding to the tissue characteristics measured in the step of examination. As such, when the treatment is performed according to the present embodiment, the tissue characteristics measured through the examination can be reflected in the tissue treatment thus enabling an effective treatment.

Figure 17:
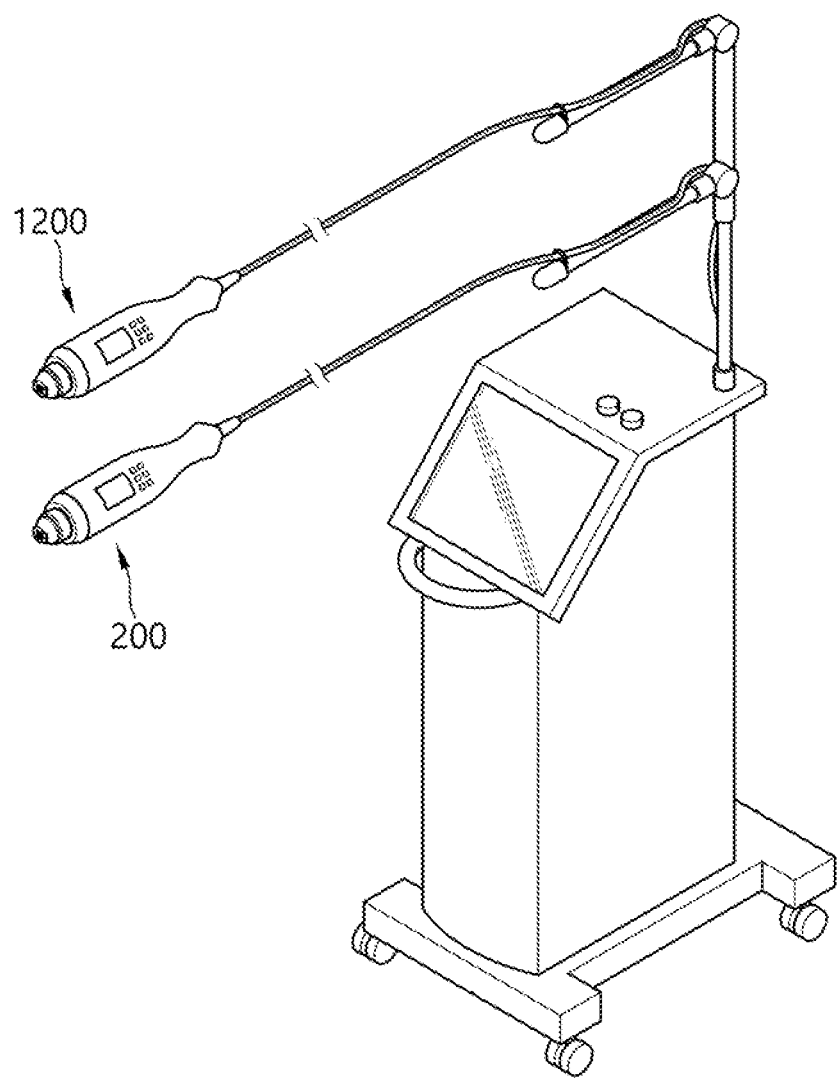
FIG. 17 is a perspective view illustrating the medical RF apparatus according to a fifth embodiment of the present invention.

FIG. 17 is a perspective view illustrating an RF treatment apparatus according to a fourth embodiment of the present invention. Hereinafter, the medical RF treatment apparatus according to a fifth embodiment of the present invention is explained with reference to FIG. 17.

In the fourth embodiment described above, the configuration was made such that the RF testing apparatus and the RF treatment apparatus were constituted as one apparatus and tissue examination and tissue treatment tissue were able to be performed using one hand piece. Compared to this, the medical RF apparatus according to the present embodiment, while the RF testing apparatus and the RF treatment apparatus are constituted as one apparatus, may be configured such that the hand piece 1200 for examination used in the step of tissue examination and the hand piece 200 for treatment used in the step of tissue treatment are provided separately. In a case where only one of the examination step and the treatment step is performed, or in a case where the types of modules used in examination and treatment or the structure of the driving unit are different, it may be advantageous to provide hand pieces separately according to the uses thereof as is the case of the present embodiment.

In this case, it is possible that examination and treatment are performed such that when a user sets the mode as an examination mode through a setting unit, the constituting elements of the main body such as a control unit and an RF generator are electrically/signally connected to the hand piece for examination, whereas when a user sets the mode as a treatment mode, it is possible that the constituting elements of the main body such as a control unit and an RF generator are electrically/signally connected to the hand piece for treatment, respectively.

Although the embodiments of the present invention has been described in detail, the present invention is not limited to the above embodiments. It will be understood by those of ordinary skill in the art that various changes and modifications in form and details may be made therein without departing from the spirit and scope of the invention as defined in the appended claims.

What is claimed is:

1. A medical RF apparatus estimating characteristics of a skin tissue with an RF pulse, comprising:
   an RF generator generating a test pulse for detecting the characteristics of the skin tissue;
   a monitoring unit monitoring a change in information on a state of the skin tissue while the test pulse is transmitted; and
   an estimating unit determining the characteristics of the skin tissue of a patient based on a time required for the skin tissue to reach a desired change while the test pulse is transmitted.

2. The medical RF apparatus of claim 1, wherein the estimating unit determines the characteristics of the skin tissue by comparing a monitored value with reference data.

3. The medical RF apparatus of claim 2, wherein the estimating unit determines the characteristics of the skin tissue based on a time required for desiccation of the skin tissue while the test pulse is transmitted.

4. The medical RF apparatus of claim 3, wherein the estimating unit determines that as the time required is longer a water content of the skin tissue is higher, whereas as the time required is shorter the water content of the skin tissue is lower.

5. The medical RF apparatus of claim 1, wherein the test pulse is transmitted in a predetermined output pattern and a pulse duration is terminated at a time point when the skin tissue reaches the desired change.

6. The medical RF apparatus of claim 1,
   wherein the monitoring unit measures a value correlated with a water content of the skin tissue while the test pulse is transmitted, and
   the estimating unit determines the characteristics of the skin tissue of the patient by comparing a measured value of the monitoring unit with reference data.

7. The medical RF apparatus of claim 1,
   wherein the monitoring unit monitors a change in impedance of the skin tissue while the test pulse is transmitted, and
   the estimating unit determines the characteristics of the skin tissue based on a time required for a monitored impedance change of the monitoring unit to reach a target value.

8. The medical RF apparatus of claim 7, wherein the estimating unit determines the characteristics of the skin tissue based on a time required until a time point when the impedance of the skin tissue increases at a rate greater than a predetermined rate of change or increases greater than a predetermined value while the test pulse is transmitted.

9. The medical RF apparatus of claim 1,
   wherein the monitoring unit monitors a change in temperature of the skin tissue while the test pulse is transmitted, and
   the estimating unit determines the characteristics of the skin tissue based on a time required for a monitored temperature change of the monitoring unit to reach a target value.

10. The medical RF apparatus of claim 1, wherein the estimating unit determines, as a characteristic of the skin tissue, a score evaluated on a health state of the skin tissue or an age of the skin tissue.

11. A medical RF apparatus for testing and treating a skin tissue, comprising:
    an RF generator, which generates a test pulse for detecting characteristics of the skin tissue and a pulse for treatment for treating the skin tissue;
    a monitoring unit, which monitors information on a state of the skin tissue while the test pulse or the pulse for treatment is transmitted;

an estimating unit, which determines the characteristics of the skin tissue of a patient based on a time required for the skin tissue to reach a desired change while the test pulse is transmitted; and a control unit, which controls parameters of the pulse for treatment by setting initial parameters of the pulse for treatment by the characteristics of the skin tissue determined in the estimating unit, followed by monitoring the information on the state of the skin tissue detected in the monitoring unit while the pulse for treatment is transmitted.

12. A method for performing an examination for a skin tissue, comprising:

transmitting a test pulse to a target site;

monitoring information on a state of the skin tissue at the target site while the test pulse is transmitted; and determining characteristics of the skin tissue of a patient based on a time required for the skin tissue to reach a desired change while the test pulse is transmitted.

13. The method of claim 12, wherein the characteristics of the skin tissue are determined based on a time required for desiccation of the skin tissue while the test pulse is transmitted.

14. The method of claim 12, wherein the monitoring is to monitor a change in impedance of the skin tissue while the test pulse is transmitted, and to determine that the desired change in the state of the skin tissue has occurred, when the impedance of the skin tissue increases at a rate greater than a predetermined rate of change or increases greater than a predetermined value.

15. The method of claim 12, wherein the determining of the characteristics is to determine that as a time required for the occurrence of the desired change in the state is longer a water content of the skin tissue is higher, whereas as the time required for the occurrence of the change in the state is shorter the water content of the skin tissue is lower.

16. The method of claim 12, wherein the transmitting of the test pulse is to transmit an RF pulse having a predetermined output pattern to the target site and maintain pulse duration until a time point when the skin tissue reaches the desired change.

17. The method of claim 12, further comprising displaying the characteristics of the skin tissue through a display unit.

18. The method of claim 12, further comprising transmitting of a pulse for treatment to the target site, wherein initial parameters for the pulse for treatment are set based on the characteristics of the skin tissue.

19. A method for controlling a medical RF apparatus, comprising:

transmitting a test pulse to a skin tissue by operating an RF generator;

determining occurrence of a desired change in a state of the skin tissue by monitoring a change in the state of the skin tissue while the test pulse is transmitted to the skin tissue; and determining characteristics of the skin tissue of a patient based on a time required for the occurrence of the desired change.

20. The method of claim 19, wherein the determining of the characteristics of the skin tissue is to determine the characteristics of the skin tissue by comparing the time required for the occurrence of the desired change with reference data.

* * * * *